US009034611B2

(12) United States Patent
Dischert et al.

(10) Patent No.: US 9,034,611 B2
(45) Date of Patent: May 19, 2015

(54) INCREASING NADPH AVAILABILITY FOR METHIONINE PRODUCTION

(75) Inventors: Wanda Dischert, Vic-le-Comte (FR); Perrine Vasseur, Martres sur Morges (FR); Cédric Boisart, Gerzat (FR); Rainer Figge, Le Crest (FR)

(73) Assignee: METALBOLIC EXPLORER, Saint Beauzire (FR)

( * ) Notice: Subject to any disclaimer, the term of this patent is extended or adjusted under 35 U.S.C. 154(b) by 14 days.

(21) Appl. No.: 13/823,696

(22) PCT Filed: Oct. 24, 2011

(86) PCT No.: PCT/EP2011/068499
§ 371 (c)(1),
(2), (4) Date: Mar. 14, 2013

(87) PCT Pub. No.: WO2012/055798
PCT Pub. Date: May 3, 2012

(65) Prior Publication Data
US 2013/0183727 A1 Jul. 18, 2013

Related U.S. Application Data

(60) Provisional application No. 61/406,249, filed on Oct. 25, 2010.

(30) Foreign Application Priority Data

Oct. 25, 2010 (EP) ..................................... 10306164

(51) Int. Cl.
*C12P 13/12* (2006.01)
*C12N 9/00* (2006.01)
*C12N 1/20* (2006.01)
*C12N 15/00* (2006.01)
*C07H 21/04* (2006.01)
*C12N 9/02* (2006.01)
*C12N 15/52* (2006.01)

(52) U.S. Cl.
CPC ............... *C12P 13/12* (2013.01); *C12N 9/0036* (2013.01); *C12N 15/52* (2013.01)

(58) Field of Classification Search
None
See application file for complete search history.

(56) References Cited

U.S. PATENT DOCUMENTS

| 8,088,620 B2 | 1/2012 | Bestel-Corre et al. |
| 2007/0087403 A1 | 4/2007 | Bestel-Corre et al. |

FOREIGN PATENT DOCUMENTS

| WO | 0210206 A2 | 2/2002 |
| WO | 03087386 A2 | 10/2003 |
| WO | 2005/007862 A2 | 1/2005 |
| WO | 2005047498 A1 | 5/2005 |
| WO | WO2005/047498 * | 5/2005 |
| WO | 2005/059155 A2 | 6/2005 |
| WO | 2005/111202 A1 | 11/2005 |
| WO | 2007020295 A2 | 2/2007 |
| WO | 2007/077041 A1 | 7/2007 |
| WO | 2007135188 A2 | 11/2007 |
| WO | 2009/043803 A2 | 4/2009 |
| WO | 2010/020681 A1 | 2/2010 |
| WO | 2011/073738 A1 | 6/2011 |

OTHER PUBLICATIONS

International Search Report for PCT/EP2011/068499 mailed Jan. 11, 2012.
Alper, H., et al. "Identifying gene targets for the metabolic engineering of lycopene biosynthesis in *Escherichia coli*," Metab. Eng. 7:155-164 (2005).
Amann, E. et al., "Vectors bearing a hybrid trp-lac promoter useful for regulated expression of cloned genes in *Escherichia coli*," Gene 25(2-3):167-178 (1983).
Amann, E. et al., "Tightly regulated tac promoter vectors useful for the expression of unfused and fused proteins in *Escherichia coli*," Gene 69(2):301-315 (1988).
Orosz, A., et al., "Analysis of the complex transcription termination region of the *Escherichia coli* rrnB gene," Eur. J. Biochem. 201(3): 653-659 (1991).
Ouzounis, C. and Karp, P., "Global Properties of the Metabolic Map of *Escherichia coli*," Genome Res. 10: 568-576 (2000).
Norrander, J., et al., "Construction of improved M13 vectors using oligodeoxynucleotide-directed mutagenesis," Gene 26:101-106 (1983).
Moreira dos Santos, M., et al., "Manipulation of malic enzyme in *Saccharomyces cervisiae* for increasing the NADPH production capacity aerobically in different cellular compartments," Metab. Eng. 6(4): 352-363 (2004).
Mermet-Bouvier, P. and Chauvat, F., "A Conditional Expression Vector for the Cyanobacteria Synechocytis sp. Strains PCC6803 and PCC6714 or *Synechococcus* sp. Strains PCC7942 and PCC6301," Current Microbiology 28:145-148 (1994).
Liebl, W., et al., "Requirement of chelating compounds for the growth of *Corynebacterium glutamicum* in synthetic medium," Appl. Microbiol. Biotechnol. 32:205-210 (1989).
Kelle, T, et al., L-lysine production; In: Eggeling, L. and Bott, M. (eds) Handbook of *Corynebacterium glutamicum*. CRC, Boca Raton, pp. 467-490 (2005).
Jackson, J., "Proton translocation of transhydrogenase," FEBS Lett. 545:18-24 (2003).

(Continued)

*Primary Examiner* — Christian Fronda
(74) *Attorney, Agent, or Firm* — Miles & Stockbridge.com

(57) ABSTRACT

The present invention is related to a microorganism for the production of methionine, wherein said microorganism is modified to enhance the transhydrogenase activity of PntAB. In a preferred aspect of the invention, the activity of the transhydrogenase UdhA is attenuated in said microorganisms. The invention also related to a method for producing methionine by fermentation.

19 Claims, No Drawings

(56) References Cited

OTHER PUBLICATIONS

Hawley, D. and McClure, W., "Compilation and analysis of *Escherichia coli* promoter DNA sequences," Nucleic Acid Res. 11(8):2237-2255 (1983).

Dennis, J. and Zylstra, G., "Plasposons: Modular Self-Cloning Minitransposon Derivatives for Rapid Genetic Analysis of Gram-Negative Bacterial Genomes," AEM, pp. 2710-2715 (Jul. 1998).

Harrington, K., et al., "Balanced branching in transcription termination," Proc. Natl. Acad. Sci. USA 98(9):5019-5024 (2001).

Datsenko, K. and Wanner, B., "One-step inactivation of chromosomal genes in *Escherichia coli* K-12 using PCR products," Proc. Natl. Acad. Sci. USA 97(12):6640-6645 (2000).

Chemler, J., et al., "Standardized biosynthesis of flavan-3-ols with effects on pancreatic beta-cell insulin secretion," Appl. Microbiol. Biotechnol. 77:797-807 (2007).

Carrier, T. and Keasling, J., "Library of Synthetic 5' Secondary Structures to Manipulate mRNA Stability in *Escherichia coli*," Biotechnol. Prog. 15:58-64 (1999).

Anderson, E., "Growth Requirements of Virus-Resistant Mutants of *Escherichia coli* Strain 'B'," Proc. Natl. Sci. Acad. USA 32:120-128 (1946).

Riedel, C., et al., "Characterization of the Phosphoenolpyruvate Carboxykinase Gene from *Corynebacterium glutamicum* and Significance of the Enzyme for Growth and Amino Acid Production," J. Mol. Microbiol. Biotechnol. 3(4):573-583 (2001).

Sanchez, A., et al., "Effect of Overexpression of a Soluble Pyridine Nucleotide Transhydrogenase (UdhA) on the Production of Poly(3-hydroxybutyrate) in *Escherichia coli*," Biotechnol. Prog. 22:420-425 (2006).

Sauer, U., et al., "The Soluble and Membrane-bound Transhydrogenases UdhA and PntAB Have Divergent Functions in NADPH Metabolism of *Escherichia coli*," JBC 279 (8):6613-6619 (2004).

Saunderson, C., "Comparative metabolism of L-methionine, DL-methionine and DL-2-hydroxy 4-methylthiobutanoic acid by broiler chicks," British Journal of Nutrition 54: 621-633 (1985).

Schaefer, U., et al., "Automated Sampling Device for Monitoring Intracellular Metabolite Dynamics," Anal. Biochem. 270: 88-96 (1999).

Tsurimoto, T., et al., "Bacteriophage Lamda Initiators: Preparation from a Strain that Overproduces the O and P Proteins," Mol. Gen. Genet. 187:79-86 (1982).

Verho, R., et al., "Engineering Redox Cofactor Regeneration for Improved Pentose Fermentation in *Saccharomyces cerevisae*," Applied and Environmental Microbiology 69(10):5892-5897 (2003).

Weckbecker, A. and Hummel, W., "Improved synthesis of chiral alcohols with *Escherichia coli* cells co-expressing pyridine nucleotide transhydrogenase, NADP+-dependent alcohol dehydrogenase and NAD+-dependent formate dehydrogenase," Biotechnology Letters 26:1739-1744 (2004).

European Search Report for European Patent Application No. EP 10 30 6164, Date of completion: Mar. 11, 2011.

* cited by examiner

INCREASING NADPH AVAILABILITY FOR METHIONINE PRODUCTION

CROSS REFERENCE TO RELATED APPLICATIONS

This application is a §371 National Stage Application of PCT/EP2011/068499, filed Oct. 24, 2011, which claims priority to European Application No. 10306164.4, filed Oct. 25, 2010, and U.S. Provisional Application No. 61/406,249, filed Oct. 25, 2010.

BACKGROUND OF THE INVENTION

1. Field of the Invention

The present invention relates to a method for increasing intracellular NADPH availability produced from NADH to enhance methionine production. Advantageously, the method for increasing levels of NADPH is associated to an increase of the one carbon metabolism to improve methionine production.

2. Description of Related Art

Sulphur-containing compounds such as cysteine, homocysteine, methionine or S-adenosylmethionine are critical to cellular metabolism and are produced industrially to be used as food or feed additives and pharmaceuticals. In particular methionine, an essential amino acid, which cannot be synthesized by animals, plays an important role in many body functions. Aside from its role in protein biosynthesis, methionine is involved in transmethylation and in the bioavailability of selenium and zinc. Methionine is also directly used as a treatment for disorders like allergy and rheumatic fever. Most of the methionine that is produced is added to animal feed.

With the decreased use of animal-derived proteins as a result of BSE and chicken flu, the demand for pure methionine has increased. Chemically D,L-methionine is commonly produced from acrolein, methyl mercaptan and hydrogen cyanide. Nevertheless the racemic mixture does not perform as well as pure L-methionine, as for example in chicken feed additives (Saunders on, C. L., (1985) British Journal of Nutrition 54, 621-633). Pure L-methionine can be produced from racemic methionine e.g. through the acylase treatment of N-acetyl-D,L-methionine, which increases production costs dramatically. The increasing demand for pure L-methionine, coupled to environmental concerns, render microbial production of methionine attractive.

The cofactor pairs NADPH/NADP$^+$ and NADH/NAD$^+$ are essential for all living organisms. They are donor and/or acceptors of reducing equivalents in many oxidation-reduction reactions in living cells. Although chemically very similar, the redox cofactors NADH and NADPH serve distinct biochemical functions and participate in more than 100 enzymatic reactions (Ouzonis, C. A., and Karp, P. D. (2000) Genome Res. 10, 568-576). Catabolic reactions are normally linked to NAD$^+$/NADH, and anabolic reactions are normally linked to NADP$^+$/NADPH. Together, these nucleotides have a direct impact on virtually every oxidation-reduction metabolic pathway in the cell.

Many industrially useful compounds require the cofactor NADPH for their biosynthesis, as for instance: production of ethanol on xylose in yeast (Verho et al., (2003) Applied and Environmental Microbiology 69, 5892-5897), high-yield production of (+)-catechins (Chemler et al., (2007) Applied and Environmental Microbiology 77, 797-807), lycopene biosynthesis in *E. coli* (Alper, H. et al., (2005) Metab. Eng. 7, 155-164) or lysine production in *Corynebacterium glutamicum* (Kelle T et al., (2005) L-lysine production; In: Eggeling L, Bott M (eds) Handbook of *corynebacterium glutamicum*. CRC, Boca Raton, pp 467-490).

The biotechnological production of L-methionine with *Escherichia coli* requires a sufficient pool of NADPH. Methionine is derived from the amino acid aspartate, but its synthesis requires the convergence of two additional pathways, cysteine biosynthesis and C1 metabolism (N-methyltetrahydrofolate). Asparate is converted into homoserine by a sequence of three reactions. Homoserine can subsequently enter the threonine/isoleucine or the methionine biosynthetic pathway.

Production of one molecule of L-methionine requires 8.5 moles of NADPH. To meet the NADPH requirement for both growth of *E. coli* and L-methionine production on minimal medium, the inventors propose here to increase the transhydrogenase activity, in the aim to increase the pool of NADPH in the cell.

The transhydrogenase reaction (below) may be catalyzed by either a membrane-bound, proton-translocating enzyme (PntAB) or a soluble, energy-independent isoform enzyme (SthA).

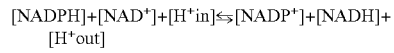

$E.$ *coli* possesses two nicotinamide nucleotide transhydrogenases encoded by the genes sthA (also called udhA) and pntAB (Sauer U. et al., 2004, *JBC*, 279:6613-6619). The physiological function of the transhydrogenases PntAB and SthA in microorganisms is the generation and the re-oxidation of NADPH, respectively (Sauer U. et al., 2004, *JBC*, 279:6613-6619). The membrane-bound transhydrogenase PntAB uses the electrochemical proton gradient as driving force for the reduction of NADP$^+$ to NADPH by oxidation of NADH to NAD$^+$ (Jackson J B, 2003, *FEBS Lett* 545:18-24).

Several strategies have been employed to improve the availability of NADPH in whole cells. Moreira dos Santos et al. (2004) report the use of NADP+-dependent malic enzymes to increase cytosolic levels of NADPH within *Saccharomyces cerevisiae*. Weckbecker and Hummel (2004) describe the overexpression of pntAB in *E. coli* to improve the NADPH-dependent conversion of acetophenone to (R)-phenylethanol. Sanchez et al. (2006) describe the overexpression of the soluble transhydrogenase SthA in *E. coli* to improve the NADPH-dependent production of poly(3-hydroxybutyrate).

The inventors have surprisingly found that, by increasing PntAB activity and reducing SthA catalyzed reaction in the bacterium, the methionine production is significantly increased.

Moreover, in combining a high transhydrogenase activity and an increase of the methylenetetrahydrofolate reductase (MetF) activity, to boost the one carbon metabolism in the cell, L-methionine production by fermentation of the modified microorganisms is greatly improved.

SUMMARY

The present invention is related to a microorganism producing methionine, wherein its production of NADPH is increased. The increase of NADPH production is achieved by increasing the PntAB transhydrogenase activity as a sole modification, or in combination with the attenuation of the activity of UdhA transhydrogenase. In a particular embodiment of the invention, the increase of NADPH production is coupled with an increase of the one carbon metabolism.

The invention is also related to a method for the production of methionine, in a fermentative process comprising the steps of:

culturing a modified methionine-producing microorganism in an appropriate culture medium comprising a source of carbon, a source of sulphur and a source of nitrogen, and recovering methionine and/or its derivatives from the culture medium, wherein in said microorganism, the transhydrogenase activity of PntAB is enhanced in a way that the production of reduced Nicotinamide Adenine Dinucleotide Phosphate (NADPH) is increased.

DETAILED DESCRIPTION OF A PREFERRED EMBODIMENT

The present invention is related to a microorganism producing methionine, wherein said microorganism is modified to enhance the transhydrogenase activity of PntAB.

The invention is also related to a method for the production of methionine in a fermentative process.

DEFINITIONS

The present invention relates to microorganisms that contain genetics modifications to enhance gene expression or protein production or activity.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

PFAM (protein families database of alignments and hidden Markov models; www.sanger.ac.uk/Software/Pfam/) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; www.ncbi.nlm.nih.gov/COG are obtained by comparing protein sequences from 66 fully sequenced genomes representing 38 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website www.ncbi.nlm.nih.gov/BLAST with the default parameters indicated on that website. The sequences obtained can then be exploited (e.g., aligned) using, for example, the programs CLUSTALW (www.ebi.ac.uk/clustalw) or MULTALIN (multalin.toulouse.inra.fr/multalin), with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989 Molecular Cloning: a Laboratory Manual. $2^{nd}$ ed. Cold Spring Harbor Lab., Cold Spring Harbor, N.Y.).

The term "attenuation of activity" according to the invention could be employed for an enzyme or a gene and denotes, in each case, the partial or complete suppression of the expression of the corresponding gene, which is then said to be 'attenuated'. This suppression of expression can be either an inhibition of the expression of the gene, a deletion of all or part of the promoter region necessary for the gene expression, a deletion in the coding region of the gene, or the exchange of the wildtype promoter by a weaker natural or synthetic promoter. Preferentially, the attenuation of a gene is essentially the complete deletion of that gene, which can be replaced by a selection marker gene that facilitates the identification, isolation and purification of the strains according to the invention. A gene is inactivated preferentially by the technique of homologous recombination (Datsenko, K. A. & Wanner, B. L. (2000) "One-step inactivation of chromosomal genes in *Escherichia coli* K-12 using PCR products". Proc. Natl. Acad. Sci. USA 97: 6640-6645).

The term "enhanced transhydrogenase PntAB activity" designates an enzymatic activity that is superior to the enzymatic activity of the non modified microorganism. The man skilled in the art knows how to measure the enzymatic activity of said enzyme. In a preferred embodiment of the invention, the PntAB activity is increased of 10% in comparison with the activity observed in a non-modified microorganism; preferentially, said activity is increased of 20%, more preferentially of 30%, even more preferentially of 50%, or is superior to 60%.

To enhance an enzymatic activity, the man skilled in the art knows different means: modifiying the catalytic site of the protein, increasing the stability of the protein, increasing the stability of the messenger RNA, increasing the expression of the gene encoding the protein.

Elements stabilizing the proteins are known in the art (for example the GST tags, Amersham Biosciences), as well as elements stabilizing the messenger RNA (Carrier and Keasling (1998) Biotechnol. Prog. 15, 58-64).

The terms "increased expression of the gene" "enhanced expression of the gene" or "overexpression of the gene" are used interchangeably in the text and have similar meaning.

To increase the expression of a gene, the man skilled in the art knows different techniques: increasing the copy-number of the gene in the microorganism, using a promoter inducing a high level of expression of the gene, attenuating the activity and/or the expression of a direct or indirect transcription repressor of the gene.

The gene is encoded chromosomally or extrachromosomally. When the gene is located on the chromosome, several copies of the gene can be introduced on the chromosome by methods of recombination known to the expert in the field (including gene replacement). When the gene is located extra-chromosomally, the gene is carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (pSC101, RK2), low copy number plasmids (pACYC, pRSF1010) or high copy number plasmids (pSK bluescript II).

In a specific embodiment of the invention, the gene is expressed using promoters with different strength. In one embodiment of the invention, the promoters are inducible. These promoters are homologous or heterologous. The man skilled in the art knows which promoters are the most convenient, for example promoters Ptrc, Ptac, Plac or the lambda promoter a are widely used.

Derivatives of Methionine:

According to the invention, methionine is recovered from the culture medium. However, it is also possible to recover from the culture medium some derivatives of methionine, that can be converted into methionine in a simple reaction. Derivatives of methionine stem from methionine transforming and/or degrading pathways such as S-acyl methionine and N-acyl methionine pathways. In particular these products are S-adenosyl-methionine (SAM) and N-acetyl-methionine (NAM). Especially NAM is an easily recoverable methionine derivative that may be isolated and transformed into methionine by deacylation.

Microorganisms

The term "microorganism for the production of methionine" or "methionine-producing microorganism" designates a microorganism producing higher levels of methionine than non-producing microorganisms, which produce methionine only for their endogenous needs. Microorganisms "optimized" for methionine production are well known in the art, and have been disclosed in particular in patent applications WO2005/111202, WO2007/077041 and WO2009/043803.

The term "modified microorganism" is related to a microorganism modified for an improved methionine production. According to the invention, the amount of methionine produced by the microorganism, and particularly the methionine yield (ratio of gram/mol methionine produced per gram/mol carbon source), is higher in the modified microorganism compared to the corresponding unmodified microorganism. Usual modifications include deletions of genes by transformation and recombination, gene replacements, and introduction of vectors for the expression of heterologous genes.

The microorganism used in the invention is a bacterium, a yeast or a fungus. Preferentially, the microorganism is selected among Enterobacteriaceae, Bacillaceae, Streptomycetaceae and Corynebacteriaceae. More preferentially, the microorganism is of the genus Escherichia, Klebsiella, Pantoea, Salmonella or Corynebacterium. Even more preferentially, the microorganism is either the species Escherichia coli or Corynebacterium glutamicum.

Increase of NADPH

According to the invention, the modified microorganism comprises, on the one hand, the modifications for an improved methionine production and, on the other hand, modifications for an improved production of available NADPH, by increasing transhydrogenase activity of PntAB.

PntAB is a transmembrane pyridine nucleotide transhydrogenase which catalyses the reduction of $NADP^+$ into NADPH via oxidation of NADH into $NAD^+$, and which is composed of two subunits alpha and beta encoded respectively by the pntA and pntB genes.

The increased activity of PntAB enhances the production of available NADPH in the cell. This does not lead automatically to an increased concentration in the cell, since available NADPH may be directly consumed by NADPH dependent enzymes. The term "increased activity of PntAB" in this context describes the increase in the intracellular activity of the transhydrogenase which is encoded by the corresponding pntA and pntB genes, for example by increasing the number of copies of the gene, using a stronger promoter or using an allele with increased activity and possibly combining these means.

In a specific embodiment of the invention, the genes encoding pntAB are overexpressed.

In a particular embodiment of the invention, the pntAB genes are overexpressed using promoters exhibiting high strength. Such promoters, for example, are those belonging to the Ptrc family which each exhibits a specific strength. The Ptrc promoter is an artificial hybrid promoter exhibiting consensus sequences of typical E. coli promoter Plac and Ptrp, in particularly the −35 box of Plac and −10 box of Ptrp (Amann et al, 1983, Gene and Amann et al, 1988, Gene). The inventors modified this artificial promoter by modifying consensus sequences of −10 or −35 boxes in accordance with promoter comparison in Hawley study (Hawley & McClure, 1983, Nucleic Acids Research) to obtain series of promoters with different strengths. The more the sequences are different from the consensus −10 and −35 boxes; the lower is the strength of the promoter. The Ptrc promoters used in the invention are named Ptrc weighted by a number: the higher is the number, the larger is the difference between the artificial promoter sequence and the consensus sequence.

In a specific embodiment of the invention, the increase of the available NADPH is obtained by increasing the activity of PntAB in combination with an attenuation of UdhA activity. UdhA is a soluble pyridine nucleotide transhydrogenase which catalyses essentially the oxidation of NADPH into $NADP^+$ via the reduction of $NAD^+$ into NADH.

As described above, the attenuation of UdhA activity may be achieved by suppressing partially or completely the corresponding udhA gene, by inhibiting the expression of the udhA gene, deleting all or part of the promoter region necessary for the gene expression, by a deletion in the coding region of the gene or by the exchange of the wildtype promoter by a weaker, natural or synthetic, promoter.

In a preferred embodiment of the invention, the attenuation of UdhA activity is achieved by a complete deletion of the udhA gene by homologous recombination.

C1 Metabolism

In a preferred embodiment of the invention, the increased production of NADPH is coupled with the increase of the one carbon metabolism (said C1 metabolism) in the methionine-producing microorganism. The C1 metabolism is well known by the man skilled in the art and is based on the folate metabolisation. The folate is reduced into dihydrofolate by folate reductase and then into tetrahydrofolate (said THF) by dihydrofolate reductase. THF is a compound involved in DNA base and amino acid biosynthesis.

THF accepts a methylene group originating from glycine or serine and forms methylene-THF. In the case of serine the transfer of the methylene group to THF is catalysed by serine hydroxymethyltransferase (GlyA) or in the case of glycine by the glycine cleavage complex (GcvTHP). The glycine-cleavage complex (GCV) is a multienzyme complex that catalyzes the oxidation of glycine, yielding carbon dioxide, ammonia, methylene-THF and a reduced pyridine nucleotide. The GCV complex consists of four protein components, the glycine dehydrogenase said P-protein (GcvP), the lipoyl-GcvH-protein said H-protein (GcvH), the aminomethyltransferase said T-protein (GcvT), and the dihydrolipoamide dehydrogenase said L-protein (GcvL or Lpd). P-protein catalyzes the pyridoxal phosphate-dependent liberation of $CO_2$ from glycine, leaving a methylamine moiety. The methylamine moiety is transferred to the lipoic acid group of the H-protein, which is bound to the P-protein prior to decarboxylation of glycine. The T-protein catalyzes the release of NH3 from the methylamine group and transfers the remaining C1 unit to THF, forming methylene-THF. The L protein then oxidizes the lipoic acid component of the H-protein and transfers the electrons to $NAD^+$, forming NADH.

In the methionine biosynthesis, methylene-THF can be reduced by methylene tetrahydrofolate reductase (MetF) to form methyl-THF. Methyl-THF is the donor of methyl during the methylation of homocysteine by the methyltransferases MetE or MetH to form methionine.

Increasing C1 metabolism leads to an improved methionine production. According to the invention, "increasing C1 metabolism" relates to the increase of the activity of at least one enzyme involved in the C1 metabolism chosen among MetF, GcvTHP, Lpd, GlyA, MetE or MetH. For increasing enzyme activity, the corresponding genes of these different enzymes may be overexpressed or modified in their nucleic sequence to expressed enzyme with improved activity or their sensitivity to feed-back regulation may be decreased.

In a preferred embodiment of the invention, the one carbon metabolism is increased by enhancing the activity of methylenetetrahydrofolate reductase MetF and/or the activity of glycine cleavage complex GcvTHP and/or the activity of serine hydroxymethyltransferase GlyA.

In a specific embodiment of the invention, the activity of MetF is enhanced by overexpressing the gene metF and/or by optimizing the translation.

In a specific embodiment of the invention, overexpression of metF gene is achieved by expressing the gene under the control of a strong promoter belonging to the Ptrc family promoters, or under the control of an inducible promoter, like a temperature inducible promoter $P_R$ as described in application PCT/FR2009/052520.

According to another embodiment of the invention, optimisation of the translation of the protein MetF is achieved by using a RNA stabiliser. Other means for the overexpression of a gene are known to the expert in the field and may be used for the overexpression of the metF gene.

Optimization of Methionine Biosynthesis Pathway:

As said above, the modified microorganism used in this invention may comprise further modifications in available NADPH production and C1 metabolism, modifications for an improved methionine production.

Genes involved in methionine production in a microorganism are well known in the art, and comprise genes involved in the methionine specific biosynthesis pathway as well as genes involved in precursor-providing pathways and genes involved in methionine consuming pathways.

Efficient production of methionine requires the optimisation of the methionine specific pathway and several precursor—providing pathways. Methionine producing strains have been described in patent applications WO2005/111202, WO2007/077041 and WO2009/043803. These applications are incorporated as reference into this application.

The patent application WO2005/111202 describes a methionine producing strain that overexpresses homoserine succinyltransferase alleles with reduced feed-back sensitivity to its inhibitors SAM and methionine. This application describes also the combination of theses alleles with a deletion of the methionine repressor MetJ responsible for the down-regulation of the methionine regulon. In addition, application describes combinations of the two modifications with the overexpression of aspartokinase/homoserine dehydrogenase.

For improving the production of methionine, the microorganism may exhibit:
an increased expression of at least one gene selected in the group consisting of:
cysP which encodes a periplasmic sulphate binding protein, as described in WO2007/077041 and in WO2009/043803,
cysU which encodes a component of sulphate ABC transporter, as described in WO2007/077041 and in WO2009/043803,
cysW which encodes a membrane bound sulphate transport protein, as described in WO2007/077041 and in WO2009/043803,
cysA which encodes a sulphate permease, as described in WO2007/077041 and in WO2009/043803,
cysM which encodes an O-acetyl serine sulfhydralase, as described in WO2007/077041 and in WO2009/043803,
cysI and cysJ encoded respectively the alpha and beta subunits of a sulfite reductase as described in WO2007/077041 and in WO2009/043803. Preferably cysI and cysJ are overexpressed together,
cysH which encodes an adenylylsulfate reductase, as described in WO2007/077041 and in WO2009/043803,
cysE which encodes a serine acyltransferase, as described in WO2007/077041,
serA which encodes a phosphoglycerate dehydrogenase, as described in WO2007/077041 and in WO2009/043803,
serB which encodes a phosphoserine phosphatase, as described in WO2007/077041 and in WO2009/043803,
serC which encodes a phosphoserine aminotransferase, as described in WO2007/077041 and in WO2009/043803,
metA alleles which encode an homoserine succinyltransferases with reduced feed-back sensitivity to S-adenosylmethionine and/or methionine as described in WO2005/111202,
thrA or thrA alleles which encode aspartokinases/homoserine dehydrogenase with reduced feed-back inhibition to threonine, as described in WO2009/043803 and WO2005/111202, or an inhibition of the expression of at least one of the following genes:
pykA which encodes a pyruvate kinase, as described in WO2007/077041 and in WO2009/043803,
pykF which encodes a pyruvate kinase, as described in WO2007/077041 and in WO2009/043803,
purU which encodes a formyltetrahydrofolate deformylase, as described in WO2007/077041 and in WO2009/043803.
yncA which encodes a N-acetyltransferase, as described in WO 2010/020681
metJ which encodes for a repressor of the methionine biosynthesis pathway, as described in WO2005/111202.

In a specific embodiment of the invention, genes may be under control of an inducible promoter. Patent application PCT/FR2009/052520 describes a methionine producing strain that expressed thrA allele with reduced feed-back inhibition to threonine and cysE under control of an inducible promoter. This application is incorporated as reference into this application.

In a preferred embodiment of the invention, thrA gene or allele is under control of a temperature inducible promoter. In a most preferred embodiment, the temperature inducible promoter used is belonging to the family of $P_R$ promoters.

In another aspect of the invention, the activity of the pyruvate carboxylase is enhanced. Increasing activity of pyruvate carboxylase is obtained by overexpressing the corresponding gene or modifying the nucleic sequence of this gene to express an enzyme with improved activity. In another embodiment of the invention, the pyc gene is introduced on the chromosome in one or several copies by recombination or carried by a plasmid present at least at one copy in the modified microorganism. The pyc gene originates from *Rhizobium* etli, *Bacillus subtilis*, *Pseudomonas fluorescens*, *Lactococcus lactis* or *Corynebacterium* species.

In a particular embodiment of the invention, the overexpressed genes are at their native position on the chromosome, or are integrated at a non-native position. For an optimal methionine production, several copies of the gene may be required, and these multiple copies are integrated into specific loci, whose modification does not have a negative impact on methionine production.

Examples for locus into which a gene may be integrated, without disturbing the metabolism of the cell, are:

| Locus | accession number | function |
| --- | --- | --- |
| aaaD | 87081759 | Pseudogene, phage terminase protein A homolog, N-terminal fragment |
| aaaE | 1787395 | Pseudogene, phage terminase protein A homolog, C-terminal fragment |
| afuB | 1786458 | Pseudogene, ferric ABC family transporter permease; C-terminal fragment |
| afuC | 87081709 | predicted ferric ABC transporter subunit (ATP-binding component) |
| agaA | 48994927 | Pseudogene, C-terminal fragment, GalNAc-6-P deacetylase |
| agaW | 1789522 | Pseudogene, N-terminal fragment, PTS system EIICGalNAc |
| alpA | 1788977 | protease |
| appY | 1786776 | DNA-binding transcriptional activator |
| argF | 1786469 | ornithine carbamoyltransferase |
| argU | none | arginine tRNA |
| argW | none | Arginine tRNA(CCU) 5 |
| arpB | 87081959 | Pseudogene reconstruction, ankyrin repeats |
| arrD | 1786768 | lysozyme |
| arrQ | 1787836 | Phage lambda lysozyme R protein homolog |
| arsB | 87082277 | arsenite transporter |
| arsC | 1789918 | arsenate reductase |
| arsR | 1789916 | DNA-binding transcriptional repressor |
| beeE | 1787397 | Pseudogene, N-terminal fragment, portal protein |
| borD | 1786770 | bacteriophage lambda Bor protein homolog |
| cohE | 1787391 | CI-like repressor |
| croE | 87081841 | Cro-like repressor |
| cspB | 1787839 | Cold shock protein |
| cspF | 1787840 | Cold shock protein homolog |
| cspI | 1787834 | Cold shock protein |
| cybC | 1790684 | Pseudogene, N-terminal fragment, cytochrome b562 |
| dicA | 1787853 | Regulatory for dicB |
| dicB | 1787857 | Control of cell division |
| dicC | 1787852 | Regulatory for dicB |
| dicF | none | DicF antisense sRNA |
| eaeH | 1786488 | Pseudogene, intimin homolog |
| efeU | 87081821 | Pseudogene reconstruction, ferrous iron permease |
| emrE | 1786755 | multidrug resistance pump |
| essD | 1786767 | predicted phage lysis protein |
| essQ | 87081934 | Phage lambda S lysis protein homolog |
| exoD | 1786750 | Pseudogene, C-terminal exonuclease fragment |
| eyeA | none | novel sRNA, unknown function |
| flu | 48994897 | Antigen 43 |
| flxA | 1787849 | Unknown |
| gapC | 87081902 | Pseudogene reconstruction, GAP dehydrogenase |
| gatR | 87082039 | Pseudogene reconstruction, repressor for gat operon |
| glvC | 1790116 | Pseudogene reconstruction |
| glvG | 1790115 | Pseudogene reconstruction, 6-phospho-beta-glucosidase |
| gnsB | 87081932 | Multicopy suppressor of secG(Cs) and fabA6(Ts) |
| gtrA | 1788691 | Bactoprenol-linked glucose translocase |
| gtrB | 1788692 | Bactoprenol glucosyl transferase |
| gtrS | 1788693 | glucosyl transferase |
| hokD | 1788745 | Small toxic membrane polypeptide |
| icd | 1787381 | Isocitrate dehydrogenase |
| icdC | 87081844 | Pseudogene |
| ilvG | 87082328 | Pseudogene reconstruction, acetohydroxy acid synthase II |
| insA | 1786204 | IS1 gene, transposition function |
| insA | 1786204 | IS1 gene, transposition function |
| insB | 1786203 | IS1 insertion sequence transposase |
| insB | 1786203 | IS1 insertion sequence transposase |
| insC | 1786557 | IS2 gene, transposition function |
| insD | 1786558 | IS2 gene, transposition function |
| insD | 1786558 | IS2 gene, transposition function |
| insE | 1786489 | IS3 gene, transposition function |
| insF | 1786490 | IS3 gene, transposition function |
| insH | 1786453 | IS5 gene, transposition function |
| insH | 1786453 | IS5 gene, transposition function |
| insH | 1786453 | IS5 gene, transposition function |
| insI | 1786450 | IS30 gene, transposition function |
| insI(−1) | 1786450 | IS30 gene, transposition function |
| insM | 87082409 | Pseudogene, truncated IS600 transposase |
| insN | 1786449 | Pseudogene reconstruction, IS911 transposase ORFAB |
| insO | none | Pseudogene reconstruction, IS911 transposase ORFAB |
| insX | 87081710 | Pseudogene IS3 family transposase, N-terminal fragment |
| insZ | 1787491 | Pseudogene reconstruction, IS4 transposase family, in ISZ' |
| intA | 1788974 | Integrase gene |
| intB | 1790722 | Pseudogene reconstruction, P4-like integrase |
| intD | 1786748 | predicted integrase |
| intE | 1787386 | e14 integrase |
| intF | 2367104 | predicted phage integrase |
| intG | 1788246 | Pseudogene, integrase homolog |
| intK | 1787850 | Pseudogene, integrase fragment |
| intQ | 1787861 | Pseudogene, integrase fragment |
| intR | 1787607 | Integrase gene |
| intS | 1788690 | Integrase |
| intZ | 1788783 | Putative integrase gene |
| isrC | none | Novel sRNA, function unknown |
| jayE | 87081842 | Pseudogene, C-terminal fragment, baseplate |
| kilR | 87081884 | Killing function of the Rac prophage |
| lafU | none | Pseudogene, lateral flagellar motor protein fragment |
| lfhA | 87081703 | Pseudogene, lateral flagellar assembly protein fragment |
| lit | 1787385 | Cell death peptidase |
| lomR | 1787632 | Pseudogene reconstruction, lom homolog; outer membrane protein interrupted by IS5Y, missing N-terminus |
| malS | 1789995 | α-amylase |
| mcrA | 1787406 | 5-methylcytosine-specific DNA binding protein |
| mdtQ | 87082057 | Pseudogene reconstruction, lipoprotein drug pump OMF family |
| melB | 1790561 | melibiose permease |
| mmuM | 1786456 | homocysteine methyltransferase |
| mmuP | 870811708 | S-methylmethionine permease |
| mokA | none | Pseudogene, overlapping regulatory peptide, enables hokB |
| ninE | 1786760 | unknown |
| nmpC | 1786765 | Pseudogene reconstruction, OM porin, interrupted by IS5B |
| nohD | 1786773 | DNA packaging protein |
| nohQ | 1787830 | Pseudogene, phage lambda Nu1 homolog, terminase small subunit family, putative DNA packaging protein |
| ogrK | 1788398 | Positive regulator of P2 growth |
| ompT | 1786777 | outer membrane protease VII |
| oweE | none | Pseudogene, lambda replication protein O homolog |
| oweS | 1788700 | Pseudogene, lambda replication protein O homolog |
| pauD | none | argU pseudogene, DLP12 prophage attachment site |
| pawZ | none | CPS-53 prophage attachment site attR, argW pseudogene |
| pbl | 87082169 | Pseudogene reconstruction, pilT homolog |
| peaD | 87081754 | Pseudogene, phage lambda replication protein P family; C-terminal fragment |
| perR | 1786448 | predicted DNA-binding transcriptional regulator |
| pgaA | 1787261 | outer membrane porin of poly-β-1,6-N-acetyl-D-glucosamine (PGA) biosynthesis pathway |
| pgaB | 1787260 | PGA N-deacetylase |
| pgaC | 1787259 | UDP-N-acetyl-D-glucosamine β-1,6-N-acetyl-D-glucosaminyl transferase |
| pgaD | 1787258 | predicted inner membrane protein |
| phnE | 87082370 | Pseudogene reconstruction, phosphonate permease |
| pinE | 1787404 | DNA invertase |

| Locus | accession number | function |
|---|---|---|
| pinH | 1789002 | Pseudogene, DNA invertase, site-specific recombination |
| pinQ | 1787827 | DNA invertase |
| pinR | 1787638 | DNA invertase |
| prfH | 1786431 | Pseudogene, protein release factor homolog |
| psaA | none | ssrA pseudogene, CP4-57 attachment site duplication |
| ptwF | none | thrW pseudogene, CP4-6 prophage attachment site |
| quuD | 1786763 | predicted antitermination protein |
| quuQ | 87081935 | Lambda Q antitermination protein homolog |
| racC | 1787614 | unknown |
| racR | 1787619 | Rac prophage repressor, cI-like |
| ralR | 1787610 | Restriction alleviation gene |
| rbsA | 1790190 | D-ribose ABC transporter subunit (ATP-binding component) |
| rbsD | 87082327 | D-ribose pyranase |
| recE | 1787612 | RecET recombinase |
| recT | 1787611 | RecET recombinase |
| relB | 1787847 | Antitoxin for RelE |
| relE | 1787846 | Sequence-specific mRNA endoribonuclease |
| rem | 1787844 | unknown |
| renD | 87081755 | Pseudogene reconstruction, lambda ren homolog, interrupted by IS3C; putative activator of lit transcription |
| rhsE | 1787728 | Pseudogene, rhs family, encoded within RhsE repeat |
| rnlA | 1788983 | RNase LS, endoribonuclease |
| rph | 1790074 | Pseudogene reconstruction, RNase PH |
| rusA | 1786762 | Endonuclease |
| rzoD | 87081757 | Probable Rz1-like lipoprotein |
| rzoQ | none | Probable Rz1-like lipoprotein |
| rzoR | 87081890 | Probable Rz1-like lipoprotein |
| rzpD | 1786769 | predicted murein endopeptidase |
| rzpQ | 1787835 | Rz-like equivalent |
| rzpR | 87081889 | Pseudogene, Rz homolog |
| sieB | 87081885 | Superinfection exclusion protein |
| sokA | none | Pseudogene, antisense sRNA blocking mokA/hokA translation |
| stfE | 87081843 | C-terminal Stf variable cassette, alternate virion-host specificity protein; Tail Collar domain, pseudogene |
| stfP | 1787400 | Predicted tail fiber protein |
| stfR | 87081892 | Side-tail fiber protein |
| tfaD | 87081759 | Pseudogene, tail fiber assembly gene, C-terminal fragment |
| tfaE | 1787402 | Predicted tail fiber assembly gene |
| tfaP | 1787401 | Predicted tail fiber assembly gene |
| tfaQ | 2367120 | Phage lambda tail fiber assembly gene homolog |
| tfaR | 1787637 | Phage lambda tail fiber assembly gene homolog |
| tfaS | 87082088 | Pseudogene, tail fiber assembly gene, C-terminal fragment |
| tfaX | 2367110 | Pseudogene reconstruction, tail fiber assembly gene, C-terminal fragment |
| thrW | none | threonine tRNA (attachment site of the CP4-6 prophage) |
| torI | 87082092 | CPS-53/KpLE1 exisionase |
| treB | 2367362 | subunit of trehalose PTS permease (IIB/IIC domains) |
| treC | 1790687 | trehalose-6-phosphate hydrolase |
| trkG | 1787626 | Major constitutive K+ uptake permease |
| ttcA | 1787607 | Integrase gene |
| ttcC | none | Pseudogene, prophage Rac integration site ttcA duplication |
| uidB | 1787902 | Glucuronide permease, inactive point mutant |
| uxaA | 1789475 | altronate hydrolase |
| uxaC | 2367192 | uronate isomerase |
| wbbL | 1788343 | Pseudogene reconstruction, rhamnosyl transferase |
| wcaM | 1788356 | predicted colanic acid biosynthesis protein |
| xisD | none | Pseudogene, exisionase fragment in defective prophage DLP12 |
| xisE | 1787387 | e14 exisionase |
| yabP | 1786242 | Pseudogene reconstruction |
| yafF | 87081701 | Pseudogene, C-terminal fragment, H repeat-associated protein |
| yafU | 1786411 | Pseudogene, C-terminal fragment |
| yafW | 1786440 | antitoxin of the YkfI-YafW toxin-antitoxin system |
| yafX | 1786442 | unknown |
| yafY | 1786445 | predicted DNA-binding transcriptional regulator; inner membrane lipoprotein |
| yafZ | 87081705 | unknown |
| yagA | 1786462 | predicted DNA-binding transcriptional regulator |
| yagB | 87081711 | Pseudogene, antitoxin-related, N-terminal fragment |
| yagE | 1786463 | predicted lyase/synthase |
| yagF | 1786464 | predicted dehydratase |
| yagG | 1786466 | putative sugar symporter |
| yagH | 1786467 | putative β-xylosidase |
| yagI | 1786468 | predicted DNA-binding transcriptional regulator |
| yagJ | 1786472 | unknown |
| yagK | 1786473 | unknown |
| yagL | 1786474 | DNA-binding protein |
| yagM | 2367101 | unknown |
| yagN | 2367102 | unknown |
| yagP | 1786476 | Pseudogene, LysR family, fragment |
| yaiT | 1786569 | Pseudogene reconstruction, autotransporter family |
| yaiX | 87082443 | Pseudogene reconstruction, interrupted by IS2A |
| ybbD | 1786709 | Pseudogene reconstruction, novel conserved family |
| ybcK | 1786756 | predicted recombinase |
| ybcL | 1786757 | predicted kinase inhibitor |
| ybcM | 1786758 | predicted DNA-binding transcriptional regulator |
| ybcN | 1786759 | DNA base-flipping protein |
| ybcO | 1786761 | unknown |
| ybcV | 87081758 | unknown |
| ybcW | 1786772 | unknown |
| ybcY | 48994878 | Pseudogene reconstruction, methyltransferase family |
| ybeM | 1786843 | Pseudogene reconstruction, putative CN hydrolase |
| ybfG | 87081771 | Pseudogene reconstruction, novel conserved family |
| ybfI | none | Pseudogene reconstruction, KdpE homolog |
| ybfL | 87081775 | Pseudogene reconstruction, H repeat-associated protein |
| ybfO | 1786921 | Pseudogene, copy of Rhs core with unique extension |
| ycgH | 87081847 | Pseudogene reconstruction |
| ycgI | 1787421 | Pseudogene reconstruction, autotransporter homolog |
| ycjV | 1787577 | Pseudogene reconstruction, malK paralog |
| ydaC | 1787609 | unknown |
| ydaE | 87081883 | Metallothionein |
| ydaF | 87081886 | unknown |
| ydaG | 87081887 | unknown |
| ydaQ | 87081882 | Putative exisionase |
| ydaS | 1787620 | unknown |
| ydaT | 1787621 | unknown |
| ydaU | 1787622 | unknown |
| ydaV | 1787623 | unknown |
| ydaW | 87081888 | Pseudogene, N-terminal fragment |
| ydaY | 1787629 | pseudogene |
| ydbA | 87081898 | Pseudogene reconstruction, autotransporter homolog |
| yddK | 1787745 | Pseudogene, C-terminal fragment, leucine-rich |
| yddL | 1787746 | Pseudogene, OmpCFN porin family, N-terminal fragment |
| ydeT | 1787782 | Pseudogene, FimD family, C-terminal fragment |
| ydfA | 1787854 | unknown |
| ydfB | 87081937 | unknown |
| ydfC | 1787856 | unknown |
| ydfD | 1787858 | unknown |
| ydfE | 1787859 | Pseudogene, N-terminal fragment |
| ydfJ | 1787824 | Pseudogene reconstruction, MFS family |
| ydfK | 1787826 | Cold shock gene |
| ydfO | 87081931 | unknown |
| ydfR | 1787837 | unknown |
| ydfU | 87081936 | unknown |
| ydfV | 1787848 | unknown |
| ydfX | 1787851 | pseudogene |
| yedN | 87082002 | Pseudogene reconstruction, IpaH/YopM family |
| yedS | 87082009 | Pseudogene reconstruction, outer membrane protein homolog |
| yeeH | none | Pseudogene, internal fragment |
| yeeL | 87082016 | Pseudogene reconstruction, glycosyltransferase family |
| yeeP | 87082019 | Pseudogene, putative GTP-binding protein |
| yeeR | 87082020 | unknown |
| yeeS | 1788312 | unknown |
| yeeT | 1788313 | unknown |
| yeeU | 1788314 | Antitoxin component of toxin-antitoxin protein pair YeeV-YeeU |
| yeeV | 1788315 | Toxin component of toxin-antitoxin protein pair YeeV-YeeU |

| Locus | accession number | function |
|---|---|---|
| yeeW | 1788316 | pseudogene |
| yegZ | none | Pseudogene, gpD phage P2-like protein D; C-terminal fragment |
| yehH | 87082046 | Pseudogene reconstruction |
| yehQ | 87082050 | Pseudogene reconstruction |
| yejO | 1788516 | Pseudogene reconstruction, autotransporter homolog |
| yfaH | 1788571 | Pseudogene reconstruction, C-terminal fragment, LysR homolog |
| yfaS | 87082066 | Pseudogene reconstruction |
| yfcU | 1788678 | Pseudogene reconstruction, FimD family |
| yfdK | 1788696 | unknown |
| yfdL | 1788697 | Pseudogene, tail fiber protein |
| yfdM | 87082089 | Pseudogene, intact gene encodes a predicted DNA adenine methyltransferase |
| yfdN | 1788699 | unknown |
| yfdP | 1788701 | unknown |
| yfdQ | 1788702 | unknown |
| yfdR | 87082090 | unknown |
| yfdS | 1788704 | unknown |
| yfdT | 1788705 | unknown |
| yffL | 1788784 | unknown |
| yffM | 1788785 | unknown |
| yffN | 1788786 | unknown |
| yffO | 1788787 | unknown |
| yffP | 1788788 | unknown |
| yffQ | 1788790 | unknown |
| yffR | 1788791 | unknown |
| yffS | 1788792 | unknown |
| yfjH | 1788976 | unknown |
| yfjI | 1788978 | unknown |
| yfjJ | 1788979 | unknown |
| yfjK | 1788980 | unknown |
| yfjL | 1788981 | unknown |
| yfjM | 1788982 | unknown |
| yfjO | 87082140 | unknown |
| yfjP | 48994902 | unknown |
| yfjQ | 1788987 | unknown |
| yfjR | 1788988 | unknown |
| yfjS | 87082142 | unknown |
| yfjT | 1788990 | unknown |
| yfjU | 1788991 | pseudogene |
| yfjV | 1788992 | Pseudogene reconstruction, arsB-like C-terminal fragment |
| yfjW | 2367146 | unknown |
| yfjX | 1788996 | unknown |
| yfjY | 1788997 | unknown |
| yfjZ | 1788998 | Antitoxin component of putative toxin-antitoxin YpjF-YfjZ |
| ygaQ | 1789007 | Pseudogene reconstruction, has alpha-amylase-related domain |
| ygaY | 1789035 | Pseudogene reconstruction, MFS family |
| ygeF | 2367169 | Pseudogene reconstruction, part of T3SS PAI ETT2 remnant |
| ygeK | 87082170 | Pseudogene reconstruction, part of T3SS PAI ETT2 remnant |
| ygeN | 1789221 | Pseudogene reconstruction, orgB homolog |
| ygeO | 1789223 | Pseudogene, orgA homolog, part of T3SS PAI ETT2 remnant |
| ygeQ | 1789226 | Pseudogene reconstruction, part of T3SS PAI ETT2 remnant |
| yghE | 1789340 | Pseudogene reconstruction, general secretion protein family |
| yghF | 1789341 | Pseudogene, general secretion protein |
| yghO | 1789354 | Pseudogene, C-terminal fragment |
| yghX | 1789373 | Pseudogene reconstruction, S9 peptidase family |
| yhcE | 1789611 | Pseudogene reconstruction, interrupted by IS5R |
| yhdW | 1789668 | Pseudogene reconstruction |
| yhiL | 87082275 | Pseudogene reconstruction, FliA regulated |
| yhiS | 1789920 | Pseudogene reconstruction, interrupted by IS5T |
| yhjQ | 1789955 | Pseudogene reconstruction |
| yibJ | 48994952 | Pseudogene reconstruction, Rhs family |
| yibS | none | Pseudogene reconstruction, Rhs family, C-terminal fragment |
| yibU | none | Pseudogene reconstruction, H repeat-associated protein |
| yibW | none | Pseudogene reconstruction, rhsA-linked |
| yicT | none | Pseudogene, N-terminal fragment |
| yifN | 2367279 | Pseudogene reconstruction |
| yjbI | 1790471 | Pseudogene reconstruction |
| yjdQ | none | Pseudogene reconstruction, P4-like integrase remnant |
| yjgX | 1790726 | Pseudogene reconstruction, EptAB family |
| yjhD | 87082406 | Pseudogene, C-terminal fragment |
| yjhE | 87082407 | Pseudogene, putative transporter remnant |
| yjhR | 1790762 | Pseudogene reconstruction, helicase family, C-terminal fragment |
| yjhV | 1790738 | Pseudogene, C-terminal fragment |
| yjhY | none | Pseudogene reconstruction, novel zinc finger family |
| yjhZ | none | Pseudogene reconstruction, rimK paralog, C-terminal fragment |
| yjiP | 1790795 | Pseudogene reconstruction, transposase family |
| yjiT | 87082428 | Pseudogene, N-terminal fragment |
| yjiV | none | Pseudogene reconstruction, helicase-like, C-terminal fragment |
| yjjN | 87082432 | predicted oxidoreductase |
| ykfA | 87081706 | putative GTP-binding protein |
| ykfB | 1786444 | unknown |
| ykfC | 87081707 | Pseudogene, retron-type reverse transcriptase family, N-terminal fragment |
| ykfF | 1786443 | unknown |
| ykfG | 2367100 | unknown |
| ykfH | 87081704 | unknown |
| ykfI | 1786439 | toxin of the YkfI-YafW toxin-antitoxin system |
| ykfJ | 1786430 | Pseudogene, N-terminal fragment |
| ykfK | 1786445 | Pseudogene, N-terminal fragment |
| ykfL | none | Pseudogene, C-terminal fragment |
| ykfN | none | Pseudogene, N-terminal remnant, YdiA family |
| ykgA | 87081714 | Pseudogene, N-terminal fragment, AraC family |
| ykgP | none | Pseudogene, oxidoreductase fragment |
| ykgQ | none | Pseudogene, C-terminal fragment of a putative dehydrogenase |
| ykgS | none | Pseudogene internal fragment |
| ykiA | 1780591 | Pseudogene reconstruction, C-terminal fragment |
| ylbE | 1786730 | Pseudogene reconstruction, yahG paralog |
| ylbG | 87081748 | Pseudogene reconstruction, discontinuous N-terminal fragment |
| ylbH | 1786708 | Pseudogene, copy of Rhs core with unique extension |
| ylbI | none | Pseudogene, internal fragment, Rhs family |
| ylcG | 87081756 | unknown |
| ylcH | none | unknown |
| ylcI | none | unknown |
| ymdE | 87081823 | Pseudogene, C-terminal fragment |
| ymfD | 1787383 | Putative SAM-dependent methyltransferase |
| ymfE | 1787384 | unknown |
| ymfI | 87081839 | unknown |
| ymfJ | 87081840 | unknown |
| ymfL | 1787393 | unknown |
| ymfM | 1787394 | unknown |
| ymfQ | 1787399 | Putative baseplate or tail fiber proteintt |
| ymfR | 1787396 | unknown |
| ymjC | none | Pseudogene, N-terminal fragment |
| ymjD | none | Expressed deletion pseudogene fusion remnant protein |
| ynaA | 1787631 | Pseudogene, N-terminal fragment |
| ynaE | 1787639 | Cold shock gene |
| ynaK | 1787628 | unknown |
| yncI | 1787731 | Pseudogene reconstruction, H repeat-associated, RhsE-linked |
| yncK | none | Pseudogene reconstruction, transposase homolog |
| yneL | 1787784 | Pseudogene reconstruction, C-terminal fragment, AraC family |
| yneO | 1787788 | Pseudogene reconstruction, putative OM autotransporter adhesi |
| ynfN | 87081933 | Cold shock gene |
| ynfO | none | unknown |
| yoeA | 87082018 | Pseudogene reconstruction, interrupted by IS2F |
| yoeD | none | Pseudogene, C-terminal fragment of a putative transposase |
| yoeF | 87082021 | Pseudogene, C-terminal fragment |
| yoeG | none | pseudogene, N-terminal fragment |
| yoeH | none | pseudogene, C-terminal fragment |
| ypdJ | 87082091 | Pseudogene, exisonase fragment |
| ypjC | 1789003 | Pseudogene reconstruction |

-continued

| Locus | accession number | function |
|---|---|---|
| ypjF | 1788999 | Toxin component of putative toxin-antitoxin pair YpjF-YfjZ |
| ypjI | none | Pseudogene reconstruction |
| ypjJ | 87082144 | unknown |
| ypjK | 87082141 | unknown |
| yqfE | 1789281 | Pseudogene reconstruction, C-terminal fragment, LysR family |
| yqiG | 48994919 | Pseudogene reconstruction, FimD family, interrupted by IS2I |
| yrdE | none | Pseudogene reconstruction, C-terminal fragment, yedZ paralog |
| yrdF | none | Pseudogene, N-terminal fragment |
| yrhA | 87082266 | Pseudogene reconstruction, interrupted by IS1E |
| yrhC | 87082273 | Pseudogene reconstruction, N-terminal fragment |
| ysaC | none | Pseudogene, C-terminal remnant |
| ysaD | none | Pseudogene, internal sequence remnant |
| ytfA | 1790650 | Pseudogene, C-terminal fragment |
| yzgL | 87082264 | Pseudogene, putative periplasmic solute binding protein |

The present invention is also related to a method for the production of methionine, comprising the steps of:
culturing a modified methionine-producing microorganism in an appropriate culture medium comprising a source of carbon, a source of sulphur and a source of nitrogen, and
recovering the methionine or one of its derivatives from the culture medium, wherein said microorganism is modified to present an enhanced transhydrogenase activity of PntAB.

Culture Conditions

The terms "fermentative process', 'culture' or 'fermentation" are used interchangeably to denote the growth of bacteria on an appropriate growth medium containing a simple carbon source, a source of sulphur and a source of nitrogen.

An appropriate culture medium is a medium appropriate for the culture and growth of the microorganism. Such media are well known in the art of fermentation of microorganisms, depending upon the microorganism to be cultured.

The term "source of carbon" according to the invention denotes any source of carbon that can be used by those skilled in the art to support the normal growth of a microorganism, which can be hexoses such as glucose, galactose or lactose; pentoses; monosaccharides; disaccharides such as sucrose, cellobiose or maltose; oligosaccharides; molasses; starch or its derivatives; hemicelluloses; glycerol and combinations thereof. An especially preferred carbon source is glucose. Another preferred carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product. Vegetal biomass, treated or not, is an interesting renewable carbon source.

The term "source of sulphur" according to the invention refers to sulphate, thiosulfate, hydrogen sulphide, dithionate, dithionite, sulphite, methylmercaptan, dimethylsulfide and other methyl capped sulphides or a combination of the different sources. More preferentially, the sulphur source in the culture medium is sulphate or thiosulfate or a mixture thereof.

The terms "source of nitrogen" corresponds to either an ammonium salt or ammoniac gas. The nitrogen source is supplied in the form of ammonium or ammoniac.

In a specific aspect of the invention, the culture is performed in such conditions that the microorganism is limited or starved for an inorganic substrate, in particular phosphate and/or potassium. Subjecting an organism to a limitation of an inorganic substrate defines a condition under which growth of the microorganisms is governed by the quantity of an inorganic chemical supplied that still permits weak growth. Starving a microorganism for an inorganic substrate defines the condition under which growth of the microorganism stops completely due, to the absence of the inorganic substrate.

The fermentation is generally conducted in fermenters with an appropriate culture medium adapted to the microorganism being used, containing at least one simple carbon source, and if necessary co-substrates for the production of metabolites.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

As an example of known culture medium for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

As an example of known culture medium for *C. glutamicum*, the culture medium can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583).

Recovering of Methionine

The action of "recovering methionine from the culture medium" designates the action of recovering methionine or one of its derivatives, in particular SAM and NAM and all other derivatives that may be useful.

The present invention is also related to a method for the production of methionine, comprising the step of isolation of methionine, its precursors or derivatives, of the fermentation broth and/or the biomass, optionally remaining in portions or in the total amount (0-100%) in the end product.

After fermentation, L-methionine, its precursors or compounds derived thereof, is/are recovered and purified if necessary. The methods for the recovery and purification of the produced compound such as methionine, S-adenosyl-methionine and N-acetyl-methionine in the culture media are well known to those skilled in the art (WO 2005/007862, WO 2005/059155).

Optionally, from 0 to 100%, preferentially at least 90%, more preferentially 95%, even more preferentially at least 99% of the biomass may be retained during the purification of the fermentation product.

Optionally, the methionine derivative N-acetyl-methionine is transformed into methionine by deacylation, before methionine is recovered.

Protocols

Several protocols have been used to construct methionine producing strains and are described in the following examples.

Protocol 1: Chromosomal Modifications by Homologous Recombination and Selection of Recombinants (Datsenko, K. A. & Wanner, B. L. (2000)

Allelic replacement or gene disruption in specified chromosomal loci was carried out by homologous recombination as described by Datsenko. & Wanner (2000). The chloramphenicol (Cm) resistance cat, the kanamycin (Km) resistance kan, or the gentamycin (Gt) resistance gm genes, flanked by Flp recognition sites, were amplified by PCR by using pKD3 or pKD4 or p34S-Gm (Dennis et Zyltra, AEM July 1998, p 2710-2715) plasmids as template respectively. The resulting PCR products were used to transform the recipient *E. coli* strain harbouring plasmid pKD46 that expresses the λ Red (λ, β, exo) recombinase. Antibiotic-resistant transformants were then selected and the chromosomal structure of the mutated loci was verified by PCR analysis with the appropriate primers listed in Table 2.

The cat, kan and gm-resistance genes were removed by using plasmid pCP20 as described by Datsenko. & Wanner (2000), except that clones harbouring the pCP20 plasmid were cultivated at 37° C. on LB and then tested for loss of antibiotic resistance at 30° C. Antibiotic sensitive clones were then verified by PCR using primers listed in Table 2

Protocol 2: Transduction of Phage P1

Chromosomal modifications were transferred to a given *E. coli* recipient strain by P1 transduction. The protocol is composed of 2 steps: (i) preparation of the phage lysate on a donor strain containing the resistance associated chromosomal modification and (ii) infection of the recipient strain by this phage lysate.

Preparation of the Phage Lysate

Inoculate 100 μl of an overnight culture of the strain MG1655 with the chromosomal modification of interest in 10 ml of LB+Cm 30 μg/ml or Km 50 μg/ml or Gt 10 μg/mL+glucose 0.2%+CaCl$_2$ 5 mM.
Incubate 30 min at 37° C. with shaking.
Add 100 μl of P1 phage lysate prepared on the donor strain MG1655 (approx. 1×10$^9$ phage/ml).
Shake at 37° C. for 3 hours until the complete lysis of cells.
Add 200 μl of chloroform, and vortex.
Centrifuge 10 min at 4500 g to eliminate cell debris.
Transfer of supernatant to a sterile tube.
Store the lysate at 4° C.
Transduction
Centrifuge 10 min at 1500 g 5 ml of an overnight culture of the *E. coli* recipient strain cultivated in LB medium.
Suspend the cell pellet in 2.5 ml of MgSO$_4$ 10 mM, CaCl$_2$ 5 mM.
Infect 100 μl al cells with 100 μl al P1 phage of strain MG1655 with the modification on the chromosome (test tube) and as a control tubes 100 μl cells without P1 phage and
100 μl P1 phage without cells.
Incubate 30 min at 30° C. without shaking.
Add 100 μl sodium citrate 1 M in each tube, and vortex.
Add 1 ml of LB.
Incubate 1 hour at 37° C. with shaking.
Centrifuge 3 min at 7000 rpm.
Plate on LB+Cm 30 μg/ml or Km 50 μg/ml or Gt 10 μg/mL
Incubate at 37° C. overnight.

The antibiotic-resistant transductants were then selected and the chromosomal structure of the mutated locus was verified by PCR analysis with the appropriate primers listed in Table 2.

TABLE 1

Genotypes and corresponding numbers of intermediate strains and producer strains that appear in the following examples.

| Strain number | Genotype |
|---|---|
| 1 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA |
| 2 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE |
| 3 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11::Cm |
| 4 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 |
| 5 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 |
| 6 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔtreBC::TT02-serA-serC::Gt |
| 7 | MG1655 metA*11 Ptrc-metH PtrcF-cysPUWAM PtrcF-cysJIH Ptrc09-gcvTHP Ptrc36-metF::Km Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔtreBC:: TT02-serA-serC::Gt |
| 8 | MG1655 metA*11 Ptrc-metH PtrcF-cysPUWAM PtrcF-cysJIH Ptrc09-gcvTHP Ptrc36-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA ::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔtreBC:: TT02-serA-serC ::Gt ΔudhA ::Km |
| 9 | MG1655 metA*11 Ptrc-metH PtrcF-cysPUWAM PtrcF-cysJIH Ptrc09-gcvTHP Ptrc36-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 DtreBC:: TT02-serA-serC :: Gt Ptrc01-pntAB::Cm ΔudhA::Km |
| 10 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 DtreBC::TT02-serA-serC |
| 11 | MG1655 metA*11 Ptrc-metH PtrcF-cysPUWAM PtrcF-cysJIH APtrc09-gcvTHP Ptrc36-RNmst17-metF Ptrc07-serB ΔmetJ ΔpykF ΔpykA ΔpurU ΔyncA ΔmalS::TTadc-CI857- |

TABLE 1-continued

Genotypes and corresponding numbers of intermediate strains and producer strains that appear in the following examples.

| Strain number | Genotype |
|---|---|
|  | PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc01-pntAB::Cm |
| 12 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc01-pntAB::Cm pCL1920-PgapA-pycRe-TT07 |
| 13 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE DpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc01-pntAB::Cm ΔudhA::Km |
| 14 | MG1655 metA*11 Ptrc-metH PtrcF-cysPUWAM PtrcF-cysJIH Ptrc09-gcvTHP Ptrc36-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc01-pntAB ::Cm ΔudhA::Km |
| 15 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc01-pntAB::Cm ΔudhA::Km pCL1920-PgapA-pycRe-TT07 |
| 16 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc01-pntAB:: ΔudhA |
| 17 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc30-pntAB::Cm ΔudhA |
| 18 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc30-pntAB::Cm ΔudhA pCL1920-PgapA-pycRe-TT07 |
| 19 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc97-pntAB::Cm ΔudhA |
| 20 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc97-pntAB::Cm ΔudhA pCL1920-PgapA-pycRe-TT07 |
| 21 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc55-pntAB::Cm ΔudhA |
| 22 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc55-pntAB::Cm ΔudhA pCL1920-PgapA-pycRe-TT07 |
| 23 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔudhA::Km |
| 24 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔudhA::Km pCL1920-PgapA-pycRe-TT07 |

TABLE 2

Primers used for PCR verifications of chromosomal modifications described above

| Genes name | Primers name | SEQ ID N° | Location of the homology with the chromosomal region | Sequences |
|---|---|---|---|---|
| malS | Ome0826-malS-F | 1 | 3734778-3734800 | GGTATTCCACGGGATTTTTCGCG |
| | Ome0827-malS-R | 2 | 3738298-3738322 | CGTCAGTAATCACATTGCCTGTTGG |
| pgaABCD | Ome 1691-DpgaABCD_verif_F | 11 | 1093002-1093020 | GGGCTGATGCTGATTGAAC |
| | Ome-1692-DpgaABCD_verif_R | 12 | 1084333-1084354 | GTGTTACCGACGCCGTAAACGG |
| uxaCA | Ome 1612-uxaCA_R3 | 15 | 3238676-3238696 | GGTGTGGTGGAAAATTCGTCG |
| | Ome 1774-DuxaCA_F | 16 | 3243726-3243707 | GCATTACGATTGCCCATACC |
| CP4-6 | Ome 1775-DCP4-6_verif_F | 22 | 259527-259546 | GCTCGCAGATGGTTGGCAAC |
| | Ome 1776-DCP4-6_verif_R | 23 | 297672-297691 | TGGAGATGATGGGCTCAGGC |
| treBC | Ome 1595-DtreB-verif_F | 27 | 4464951-4464930 | GTTGCCGAACATTTGGGAGTGC |
| | Ome1596-DtreB_verif_R | 28 | 4462115-4462136 | GGAGATCAGATTCACCACATCC |
| metF | Ome0726-PtrcmetF F | 29 | 4130309-4130337 | GCCCGGTACTCATGTTTTCGGGTTTATGG |
| | Ome0727 PtrcmetF R | 30 | 4130967-4130940 | CCGTTATTCCAGTAGTCGCGTGCAATGG |
| udhA | Oag0055-udhAF2 | 33 | 4159070-4159053 | GTGAATGAACGGTAACGC |
| | Oag0056-udhAR2 | 34 | 4157088-4157107 | GATGCTGGAAGATGGTCACT |
| pntAB | Ome1151-pntAF | 37 | 1676137-1676118 | CCACTATCACGGCTGAATCG |
| | Ome1152-pntAR | 38 | 1675668-1675687 | GTCCCAGGATTCAGTAACGC |
| wcaM | Ome1707-DwcaM_verif_F | 43 | 2115741-2115762 | GCCGTTCAACACTGGCTGGACG |
| | Ome1708-DwcaM_verif_R | 44 | 2110888-2110907 | TGCCATTGCAGGTGCATCGC |

I. Example 1

Construction of strain 7, MG1655 metA*11 Ptrc-metH PtrcF-cysPUWAM PtrcF-cysJIH Ptrc09-gcvTHP Ptrc36-metF::Km Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔtreBC::TT02-serA-serC::Gt

I.1. Construction of Strain 1

Methionine producing strain 1 (Table 1) has been described in patent application WO2007/077041 which is incorporated as reference into this application.

I.2. Construction of Strain 2

The TTadc-CI857-PlambdaR*(-35)-thrA*1-cysE fragment was inserted at the malS locus in two steps. First the plasmid pUC18-DmalS::TTadc-C1857-PlambdaR*(-35)-thrA*1-cysE::Km was constructed and second the TTadc-CI857-PlambdaR*(-35)-thrA*1-cysE::Km fragment containing upstream and downstream sequences homologous to malS locus was introduced into the chromosome. Subsequently, the resistance cassette was removed according to Protocol 1.

All descriptions of integrations at different loci on the chromosome presented below are following the same method; 1) construction of duplication vector containing upstream and downstream homologous sequence of the locus of interest, the DNA fragment and a resistance cassette 2) construction of minimal strain (MG1655) containing the chromosomal modification of interest and 3) transduction into the complex strain (MG1655 containing already several modifications).

I.2.1. Construction of pUC18-ΔmalS::TTadc-CI857-PlambdaR*(-35)-thrA*1-cysE::Km Plasmid The plasmid pUC18-ΔmalS::TTadc-C1857-PlambdaR*(-35)-thrA*1-cysE is derived from plasmids pSCB-TTadc-c1857-PlambdaR*(-35)-thrA*1-cysE and pUC18-ΔmalS::MCS::Km that have been described in patent application PCT/FR2009/052520. Briefly, the ApaI/BamHI digested TTadc-c1857-PlambdaR*(-35)-thrA*1-cysE fragment was cloned between the ApaI and BamHI sites of the pUC18-ΔmalS::MCS-Km. The resulting plasmid was verified by DNA sequencing and called pUC18-ΔmalS::TTadc-C1857-PlambdaR*(-35)-thrA*1-cysE::Km.

I.2.2. Construction of Strain MG1655 metA*11 ΔmalS::TTadc-C1857-PlambdaR*(-35)-thrA*1-cysE::Km (pKD46)

To replace the malS gene by the TTadc-C1857-PlambdaR*(-35)-thrA*1-cysE::Km DNA fragment, pUC18-DmalS::TTadc-C1857-PlambdaR*(-35)-thrA*1-cysE::Km was digested by ScaI and EcoRV and the remaining digested fragment TTadc-CI857-PlambdaR*(-35)-thrA*1-cysE::Km containing upstream and downstream sequence homologous to the malS locus was introduced into the strain MG1655 metA*11 pKD46 according to Protocol 1. Kanamycin resistant recombinants were selected and the presence of the ΔmalS::TTadc-CI857-PlambdaR*(-35)-thrA*1-cysE::Km chromosomal modification was verified by PCR with primers Ome 0826-malS-F (SEQ ID No 1) and Ome 0827-malS-R (SEQ ID No 2) (Table 2) and by DNA sequencing. The verified and selected strain was called MG1655 metA*11 pKD46 ΔmalS::TTadc-CI857-PlambdaR*(-35)-thrA*1-cysE::Km.

I.2.3. Transduction of ΔmalS::TTadc-C1857-PlambdaR*(-35)-thrA*1-cysE::Km into strain 1 and removal of resistance cassette The ΔmalS::TTadc-CI857-PlambdaR*(-35)-thrA*1-cysE::Km chromosomal modification was transduced into the strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykA ΔpurU ΔyncA with a P1 phage lysate from strain MG1655 metA*11 pKD46 ΔmalS::TTadc-CI857-PlambdaR*(-35)-thrA*1-cysE::Km described above, according to Protocol 2.

Kanamycin resistant transductants were selected and the presence of ΔmalS::TTadc-CI857-PlambdaR*(-35)-thrA*1-cysE::Km chromosomal modification was verified by PCR with primers Ome 0826-malS-F (SEQ ID No 1) and Ome 0827-malS-R (SEQ ID No 2) (Table 2). The resulting strain has the genotype MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE::Km Finally, the kanamycin resistance of the above strain was removed according to Protocol 1. The loss of the kanamycin resistant cassette was verified by PCR by using the primers Ome 0826-malS-F (SEQ ID No 1) and Ome 0827-malS-R (SEQ ID No 2) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS:: TTadc-CI857-PlambdaR*(-35)-thrA*1-cysE was called strain 2.

I.3. Construction of Strain 3

I.3.1. Construction of the plasmid pUC18-ΔpgaABCD::TT02-TTadc-PlambdaR*(-35)-RBS01-thrA*1-cysE-PgapA-metA*11::Cm Plasmid pUC18-ΔpgaABCD::TT02-TTadc-PlambdaR*(-35)-RBS01-thrA*1-cysE-PgapA-metA*11::Cm is derived from plasmids pCL1920-TTadc-PlambdaR*(-35)-RBS01-thrA*1-cysE-PgapA-metA*11 and pUC18-ΔpgaABCD::TT02-MCS::Cm described below. Construction of Plasmid pCL1920-TTadc-PlambdaR*(-35)-RBS01-thrA*1-cvsE-PgapA-metA*11

Plasmid pCL1920-TTadc-PlambdaR*(-35)-RBS01-thrA*1-cysE-PgapA-metA*11 is derived from plasmid pCL1920-TTadc-CI857-PlambdaR*(-35)-thrA*1-cysE-PgapA-metA*11 described in patent application PCT/FR2009/052520.

To construct plasmid pCL1920-TTadc-PlambdaR*(-35)-RBS01-thrA*1-cysE-PgapA-metA*11, plasmid pCL1920-TTadc-CI857-PlambdaR*(-35)-thrA*1-cysE-PgapA-metA*11 was amplified with primers PR-RBS01_F (SEQ ID No 3) and TTadc-pCL1920_R (SEQ ID No 4). The PCR product was digested by DpnI in order to eliminate the parental DNA template. The remaining cohesive overhang was phosphorylated and introduced in an E. coli strain to form plasmid pCL1920-TTadc-PlambdaR*(-35)-RBS01-thrA*1-cysE-PgapA-metA*11. The TTadc-PlambdaR*(-35)-RBS01-thrA*1-cysE-PgapA-metA*11 insert and especially the presence of the RBS01 sequence upstream of the thrA gene were verified by DNA sequencing, using the following primers.

PR-RBS01_F
(SEQ ID N°3)
ACGTTAAATCTATCACCGCAAGGGATAAATATCTAACACCGTGCGTGTTG

ACAATTTTACCTCTGGCGGTGATAATGGTTGCATGTAC<u>TAAGGAGGTTAT</u>

<u>AA</u>ATGAGAGTGTTGAAGTTCGG with upper case sequence homologous to lambda bacteriophage P<sub>R</sub> promoter (PlambdaR*(-35), (Mermet-Bouvier & Chauvat, 1994, Current Microbiology, vol. 28, pp 145-148; Tsurimoto T, Hase T, Matsubara H, Matsubara K, Mol Gen Genet. 1982; 187(1):79-86).

underlined upper case sequence corresponding to RBS01 sequence with a PsiI restriction site bold upper case sequence homologous to 5' end of thrA (1-20)

TTadc-pCL1920_R
(SEQ ID N°4)
TAAAAAAAATAAGAGTTACCATTTAAGGTAACTCTTATTTTTAGGGCCCG

GTACCCAGCTTTTGTTCCCTTTAGTGAGGGTTAATTGC with upper case sequence homologous to TTadc transcriptional terminator sequence (transcription terminator of the adc gene from Clostridium acetobutylicum, homologous from 179847 to 179807 of the pSLO1 megaplasmid).

bold upper case sequence homologous to pCL1920-TTadc-CI857-PlambdaR*(-35)-thrA*1-cysE-PgapA-metA*11 plasmid Construction of pUC18-ΔpgaABCD::TT02-MCS::Cm Plasmid To construct the ΔpgaABCD::TT02-MCS::Cm fragment, the upstream region of pgaA (uppgaA), the TT02 transcriptional terminator, the multiple cloning site (MCS) and the downstream region of pgaD (downpgaD) were joined by PCR. The chloramphenicol cassette (Cm) was subsequently amplified and added to the previous construct. First, the uppgaA-TT02 was amplified from E. coli MG1655 genomic DNA using primers Ome 1687-ΔpgaABCD_amont_EcoRI_F (SEQ ID No 5) and Ome 1688-ΔpgaABCD_amont_TT02_BstZ17I_R (SEQ ID No 6) by PCR. Then, the TT02-MCS-down-pgaD fragment was amplified from E. coli MG1655 genomic DNA using primers Ome 1689-ΔpgaABCD_aval_MCS_BstZ17I_F (SEQ ID No 7) and Ome 1690-ΔpgaABCD_aval_EcoRI_R (SEQ ID No 8) by PCR. Primers Ome 1688-ΔpgaABCD_amont_TT02_BstZ17I_R (SEQ ID No 6) and Ome 1689-ΔpgaABCD_avalMCS_BstZ17I_F (SEQ ID No 7) have been designed to overlap through a 36 nucleotides-long region. Finally, the uppgaA-TT02-MCS-downpgaD fragment was amplified by mixing the uppgaA-TT02 and the TT02-MCS-down-pgaD amplification products using primers Ome 1687-ΔpgaABCD_amont_EcoRI_F (SEQ ID No 5) and Ome 1690-ΔpgaABCD_aval_EcoRI_R (SEQ ID No 8). The resulting fusion PCR product was digested by HpaI and cloned between the HindIII and EcoRI of pUC18 plasmid that had been treated by Large (Klenow) Fragment of E. coli DNA Polymerase I. The resulting plasmid was verified by DNA sequencing and called pUC18-ΔpgaABCD::TT02-MCS.

Ome 1687-ΔpgaABCD_amont_EcoRI_F
(SEQ ID N°5)
CGTAGTTAACGAATTCGACTAGAAAGTATGTGAGCAACTATCGGCCCCC with
- bold upper case sequence for HpaI and EcoRI restriction site and extrabases,
- upper case sequence homologous to sequence upstream pgaA gene (1092609-1092576, reference sequence on the website ecogene.org)

Ome 1688-ΔApgaABCD_amont_TT02_BstZ17I_R
(SEQ ID N°6)
GCTTGTATACAACAGATAAAACGAAAGGCCCAGTCTTTCGACTGAGCCTT TCGTTTTATTTGATGAGGCTGCGCTACGGCACTCACGG with
- bold upper case sequence for BstZ17I restriction site and extrabases,
  - underlined upper case sequence corresponding to the transcriptional terminator $T_1$ of *E. coli* rrnB (Orosz A, Boros I and Venetianer P. Eur. J. Biochem. 1991 Nov. 1; 201(3):653-9)
- upper case sequence homologous to sequence upstream pgaA gene (1091829-1091851, reference sequence on the website ecogene.org)

Ome 1689-ΔpgaABCD_aval_MCS_BstZ17I_F
(SEQ ID N°7)
AGACTGGGCCTTTCGTTTTATCTGTTGTATACAAGCTTAATTAAGGGCCC GGGCGGATCCCCCAAAACAAAGCCCGGTTCGC with
- bold upper case sequence complementary to the 3' end sequence of the transcriptional terminator $T_1$ of *E. coli* rrnB (Orosz A, Boros I and Venetianer P. Eur. J. Biochem. 1991 Nov. 1; 201(3):653-9),
- underlined upper case sequence containing a MCS multiple cloning site: BstZ17I, HindIII, PacI, ApaI, BamHI,
- upper case sequence homologous to sequence upstream of the pgaD gene (1085325-1085304, reference sequence on the website ecogene.org)

Ome 1690-ΔpgaABCD_aval_EcoRI_R
(SEQ ID N°8)
CGTAGTTAACGAATTCAGCTGATATTCGCCACGGGC with
- bold upper case sequence for HpaI and EcoRI restriction sites and extrabases,
- upper case sequence homologous to sequence upstream of the pgaD gene (1084714-1084733, reference sequence on the website ecogene.org)

Finally, primers Ome 1603-K7_Cm_ampl_SmaI_BstZ17I_F (SEQ ID No 9) and Ome 1604-K7_Cm_ampl_HindIII_R (SEQ ID No 10) were used to amplify the chloramphenicol cassette and the FRT sequences from plasmid pKD3 and the fragment was cloned between the BstZ17I and HindIII sites of plasmid pUC18-ΔpgaABCD::TT02-MCS. The resulting plasmid was verified by DNA sequencing and called pUC18-ΔpgaABCD::TT02-MCS::Cm.

Ome 1603-K7_Cm_ampl_SmaI_BstZ17I_F
(SEQ ID N°9)
TCCCCCGGGGTATACTGTAGGCTGGAGCTGCTTCG With
- underlined upper case sequence for BstZ17I and SmaI restriction site and extrabases,
- upper case sequence corresponding to site primer 1 of plasmid pKD3 (Datsenko, K. A. & Wanner, B. L., 2000, PNAS, 97: 6640-6645)

Ome 1604-K7_Cm_ampl_HindIII_R
(SEQ ID N°10)
GCCCAAGCTTCATATGAATATCCTCCTTAG with
- underlined upper case sequence HindIII restriction site and extrabases,
- upper case sequence corresponding to site primer 2 of pKD3 plasmid (Datsenko, K. A. & Wanner, B. L., 2000, PNAS, 97: 6640-6645).

Construction of the pUC18-ΔpgaABCD::TT02-TTadc-PlambdaR*(-35)-RBS01-thrA*1-cvsE-PgapA-metA*11::Cm To construct pUC18-ΔpgaABCD::TT02-TTadc-PlambdaR*(-35)-RBS01-thrA*1-cysE-PgapA-metA*11::Cm, the ApaI/BamHI fragment TTadc-PlambdaR*(-35)-RBS01-thrA*1-cysE-PgapA-metA*11 isolated from pCL1920-TTadc-PlambdaR*(-35)-RBS01-thrA*1-cysE-PgapA-metA*11 described above was cloned between the ApaI and BamHI sites of plasmid pUC18-ΔpgaABCD::TT02-MCS::Cm described above. The resulting plasmid was verified by DNA sequencing and called pUC18-ΔpgaABCD::TT02-TTadc-PlambdaR*(-35)-RBS01-thrA*1-cysE-PgapA-metA*11::Cm.

I.3.2. Construction of strain MG1655 metA*11 ΔpgaABCD::TT02-TTadc-PlambdaR*(-35)-RBS01-thrA*1-cysE-PgapA-metA*11::Cm (pKD46)

To replace the pgaABCD operon by the TT02-TTadc-PlambdaR*(-35)-RBS01-thrA*1-cysE-PgapA-metA*11::Cm region, pUC18-ΔpgaABCD::TT02-TTadc-PlambdaR*(-35)-RBS01-thrA*1-cysE-PgapA-metA*11::Cm was digested by SapI and AatII restriction enzymes and the remaining digested fragment ΔpgaABCD::TT02-TTadc-PlambdaR*(-35)-RBS01-thrA*1-cysE-PgapA-metA*11::Cm was introduced into strain MG1655 metA*11 pKD46 according to Protocol 1.

Chloramphenicol resistant recombinants were selected and the presence of the ΔpgaABCD::TT02-TTadc-PlambdaR*(-35)-RBS01-thrA*1-cysE-PgapA-metA*11:: Cm chromosomal modification was verified by PCR with primers Ome 1691-DpgaABCD_verif_F (SEQ ID No 11) and Ome 1692-DpgaABCD_verif_R (SEQ ID No 12) (Table 2) and by DNA sequencing. The verified and selected strain was called MG1655 metA*11 ΔpgaABCD::TT02-TTadc-PlambdaR*(-35)-RBS01-thrA*1-cysE-PgapA-metA*11::Cm (pKD46).

I.3.3. Transduction of ΔpgaABCD::TT02-TTadc-PlambdaR*(-35)-RBS01-thrA*1-cysE-PgapA-metA*11:: Cm into strain 2

The ΔpgaABCD::TT02-TTadc-PlambdaR*(-35)-RBS01-thrA*1-cysE-PgapA-metA*11:: Cm chromosomal modification was transduced into strain 2 (Table 1), described above, with a P1 phage lysate from strain MG1655 metA*11 pKD46 ΔpgaABCD::TT02-TTadc-PlambdaR*(-35)-RBS01-thrA*1-cysE-PgapA-metA*11::Cm described above, according to Protocol 2.

Chloramphenicol resistant transductants were selected and the presence of the ΔpgaABCD::TT02-TTadc-PlambdaR*(-35)-RBS01-thrA*1-cysE-PgapA-metA*11:: Cm chromosomal modification was verified by PCR with Ome 1691-DpgaABCD_verif_F (SEQ ID No 11) and Ome 1692-DpgaABCD_verif_R (SEQ ID No 12) (Table 2). The resulting strain MG1655 metA*11 Ptrc-metH PtrcF-cysPUWAM PtrcF-cysJIH Ptrc09-gcyTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11::Cm was called strain 3.

I.4. Construction of Strain 4

I.4.1. Construction of pUC18-ΔuxaCA::TT07-TTadc-PlambdaR*(-35)-RBS01-thrA*1-cysE-PgapA-metA*11:: Km Plasmid To construct the plasmid pUC18-ΔuxaCA::TT07-MCS-Km, the ΔuxaCA::TT07-MCS-Km fragment was obtained by PCR using the *E. coli* MG1655 ΔuxaCA::TT07-MCS-Km genomic DNA as template and cloned into pUC18 (Norrander et al., 1983, *Gene* 26, 101-106).

Construction of Strain MG1655 ΔuxaCA::TT07-MCS-Km pKD46

To replace the uxaCA region by the TT07-MCS-Km fragment, Protocol 1 was used except that primers Ome 1506-DuxaCA-MCS-F (SEQ ID No 13) and Ome 1507-DuxaCA-MCS-R (SEQ ID No 14) were used to amplify the kanamycin resistance cassette from pKD4 plasmid.

Ome 1506-DuxaCA-MCS-F
(SEQ ID N°13)
*GCAAGCTAGCTCACTCGTTGAGAGGAAGACGAAAATGACTCCGTTTATGA*

*CTGAAGATTTCCTGTTAGATACCG*TCACACTGGCTCACCTTCGGGTGGGC

CTTTCTGCTGTAGGCTGGAGCTGCTTCG with
italic upper case sequence homologous to sequence upstream uxaCA locus (3242797-3242724, reference sequence on the website ecogene.org),
underlined upper case sequence for T7Te transcriptional terminator sequence from phage T7 (Harrington K. J., Laughlin R. B. and Liang S. Proc Natl Acad Sci USA. 2001 Apr. 24; 98(9):5019-24.),
upper case sequence corresponding to primer site 2 of plasmid pKD4 (Datsenko, K. A. & Wanner, B. L., 2000, PNAS, 97: 6640-6645).

Ome 1507-DuxaCA-MCS-R
(SEQ ID N°14)
*TTAACAACTCATTTCGACTTTATAGCGTTACGCCGCTTTTGAAGATCGCC*

GAATTCGAGCTCGGTACCCGGGGATCCATCTCGAGATCCGCGGATGTATA

CATGGGCCCCATATGAATATCCTCCTTAG with
italic upper case sequence homologous to sequence downstream of the uxaCA locus (3239830-3239879, reference sequence on the website ecogene.org),
a region (underlined upper case) for the MCS containing the sequence of the restriction sites ApaI, BstZ17I, SacII, XhoI, AvaI, BamHIII, SmaI, KpnI, SacI, EcoRI,
upper case corresponding to primer site 1 of plasmid pKD4 (Datsenko, K. A. & Wanner, B. L., 2000, PNAS, 97: 6640-6645), Kanamycin resistant recombinants were selected and the insertion of the resistance cassette was verified by PCR with primers Ome 1612-uxaCA_R3 (SEQ ID No 15) and Ome 1774-DuxaCA_F (SEQ ID No 16) (Table 2) and by DNA sequencing. The verified and selected strain was called MG1655 ΔuxaCA::TT07-MCS-Km pKD46.

Construction of Plasmid pUC18-ΔuxaCA::TT07-MCS::Km

The ΔuxaCA::TT07-MCS-Km region was amplified by PCR from *E. coli* MG1655 ΔuxaCA::TT07-MCS-Km genomic DNA described above as template with primers Ome 1515-uxaCA-R2 (SEQ ID No 17) and Ome 1516-uxaCA-F2 (SEQ ID No 18).

Ome 1515-uxaCA R2 (SEQ ID No 17)
CCCACTGGCCTGTAATATGTTCGG, homologous to sequence downstream uxaCA locus (3239021-3239044)

Ome 1516-uxaCA F2
(SEQ ID N°18)
ATGCGATATCGACCGTATAAGCAGCAGAATAGGC with
underlined upper case sequence for the restriction site EcoRV and extra-bases
italic upper case sequence homologous to the sequence upstream of the uxaCA locus (3243425-3243402)

Then, the resulting PCR product (obtained with a blunt-end DNA polymerase) was digested by the restriction enzyme EcoRV and cloned into the SmaI site of pUC18. The resulting plasmid was verified by DNA sequencing and called pUC18-ΔuxaCA::TT07-MCS-Km.

Construction of pUC18-ΔuxaCA-TT07-TTadc-PlambdaR*(-35)-RBS01-thrA*1-cysE-PgapA-metA*11::Km To construct pUC18-ΔuxaCA-TT07-TTadc-PlambdaR*(-35)-RBS01-thrA*1-cysE-PgapA-metA*11::Km, the TTadc-PlambdaR*(-35)-RBS01-thrA*1-cysE-PgapA-metA*11 ApaI/BamHI digested fragment from pCL1920-TTadc-PlambdaR*(-35)-RBS01-thrA*1-cysE-PgapA-metA*11 described above was cloned into the ApaI and BamHI sites of pUC18-ΔuxaCA::TT07-MCS-Km described above. The resulting plasmid was verified by DNA sequencing and called pUC18-ΔuxaCA-TT07-TTadc-PlambdaR*(-35)-RBS0'-thrA*1-cysE-PgapA-metA*11::Km I.4.2. Construction of Strain MG1655 metA*11 ΔuxaCA:: TT07-TTadc-PlambdaR*(-35)-RBS01-thrA*1-cysE-PgapA-metA*11 (pKD46)

To replace the uxaCA operon by the TT07-TTadc-PlambdaR*(-35)-RBS01-thrA*1-cysE-PgapA-metA*11::Km region, pUC18-ΔuxaCA::TT07-TTadc-PlambdaR*(-35)-RBS01-thrA*1-cysE-PgapA-metA*11::Km was digested by BamHI and AhdI and the remaining digested fragment ΔuxaCA::TT07-TTadc-PlambdaR*(-35)-RBS01-thrA*1-cysE-PgapA-metA*11::Km was introduced into strain MG1655 metA*11 pKD46 according to Protocol 1.

Kanamycin resistant recombinants were selected and the presence of the ΔuxaCA::TT07-TTadc-PlambdaR*(-35)-RBS01-thrA*1-cysE-PgapA-metA*11::Km chromosomal modification was verified by PCR with primers Ome 1612-uxaCA_R3 (SEQ ID No 15) and Ome 1774-DuxaCA_F (SEQ ID No 16) (Table 2) and by DNA sequencing. The resulting strain was designated MG1655 metA*11 ΔuxaCA:: TT07-TTadc-PlambdaR*(-35)-RBS01-thrA*1-cysE-PgapA-metA*11::Km (pKD46)

I.4.3. Transduction of ΔuxaCA::TT07-TTadc-PlambdaR*(-35)-RBS01-thrA*1-cysE-PgapA-metA*11::Km into Strain 3

The ΔuxaCA::TT07-TTadc-PlambdaR*(-35)-RBS01-thrA*1-cysE-PgapA-metA*11::Km chromosomal modification was transduced into strain 3 (Table 1), described above, with a P1 phage lysate from strain MG1655 metA*11 pKD46 ΔuxaCA::TT07-TTadc-PlambdaR*(-35)-RBS01-thrA*1-cysE-PgapA-metA*11::Km described above, according to Protocol 2.

The ΔuxaCA::TT07-TTadc-PlambdaR*(-35)-RBS01-thrA*1-cysE-PgapA-metA*11::Km chromosomal modification was verified by PCR with Ome 1612-uxaCA_R3 (SEQ ID No 15) and Ome 1774-DuxaCA_F (SEQ ID No 16) (Table 2). The resulting strain was called MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11:: Cm ΔuxaCA::TT07-TTadc-PlambdaR*(-35)-RBS01-thrA*1-cysE-PgapA-metA*11::Km Finally, the chloramphenicol and kanamycin resistance cassettes of the above strain were removed according to Protocol 1. The loss of the chloramphenicol and kanamycin resistance cassettes was verified by PCR with primers Ome 1691-DpgaABCD_verif_F (SEQ ID No 11), Ome 1692-DpgaABCD_verif_R (SEQ ID No 12), Ome 1612-uxaCA_R3 (SEQ ID No 15) and Ome 1774-DuxaCA_F (SEQ ID No 16) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 was called strain 4.

I.5. Construction of Strain 5

I.5.1. Construction of Plasmid pMA-DCP4-6::TT02-TTadc-PlambdaR*(-35)-thrA*1-cysE-PgapA-metA*11::Km Plasmid pMA-ΔCP4-6::TT02-TTadc-PlambdaR*(-35)-thrA*1-cysE-PgapA-metA*11::Km is derived from pCL1920-TTadc-PlambdaR*(-35)-RBS01-thrA*1-cysE-PgapA-metA*11 described above and pMA-ΔCP4-6::TT02-MCS::Km described below. Construction of plasmid pMA-ΔCP4-6::TT02-MCS::Km First pMA-ΔCP4-6::TT02-MCS was synthesized by GeneArt (www.geneart.com). The ΔCP4-6::TT02-MCS fragment was cloned into the AscI and PacI sites of plasmid pMA from GeneArt and contains the following sequence identified as SEQ ID No 19:

```
ggcgcgccaggcctagggCCGACGATGTACGTCAGGTGTGCAACCTCGCCGATCCGGTG
GGGCAGGTAATCGATGGCGGCGTACTGGACAGCGGCCTGCGTCTTGAGCGTCG
TCGCGTACCGCTGGGGGTTATTGGCGTGATTTATGAAGCGCGCCCGAACGTGA
CGGTTGATGTCGCTTCGCTGTGCCTGAAAACCGGTAATGCGGTGATCCTGCGC
GGTGGCAAAGAAACGTGTCGCACTAACGCTGCAACGGTGGCGGTGATTCAGG
ACGCCCTGAAATCCTGCGGCTTACCGGCGGGTGCCGTGCAGGCGATTGATAAT
CCTGACCGTGCGCTGGTCAGTGAAATGCTGCGTATGGATAAATACATCGACAT
GCTGATCCCGCGTGGTGGCGCTGGTTTGCATAAACTGTGCCGTGAACAGTCGA
CAATCCCGGTGATCACAGGTGGTATAGGCGTATGCCATATTTACGTTGATGAA
AGTGTAGAGATCGCTGAAGCATTAAAAGTGATCGTCAACGCGAAAACTCAGCG
TCCGAGCACATGTAATACGGTTGAAACGTTGCTGGTGAATAAAAACATCGCCG
ATAGCTTCCTGCCCGCATTAAGCAAACAAATGGCGGAAAGCGGCGTGACATTA
CACGCAGATGCAGCTGCACTGGCGCAGTTGCAGGCAGGCCCTGCGAAGGTGGT
TGCTGTTAAAGCCGAAGAGTATGACGATGAGTTTCTGTCATTAGATTTGAACGT
CAAAATCGTCAGCGATCTTGACGATGCCATCGCCCATATTCGTGAACACGGCA
CACAACACTCCGATGCGATCCTGACCCGCGATATGCGCAACGCCCAGCGTTTT
GTTAACGAAGTGGATTCGTCCGCTGTTTACGTTAACGCCTCTACGCGTTTTACC
GACGGCGGCCAGTTTGGTCTGGGTGCGGAAGTGGCGGTAAGCACACAAAAAC
TCCACGCGCGTGGCCCAATGGGGCTGGAAGCACTGACCACTTACAAGTGGATC
GGCATTGGTGATTACACCATTCGTGCGTAACATCAAATAAAACGAAAGGCTC
AGTCGAAAGACTGGGCCTTTCGTTTTATCTGTTGTATACAAGCTTAATAAGGG
CCCGGGCGGATCCCACCACGTTTCCTCCTGTGCCGTATTTGTGCCATTGTAACC
TTGGCAATTCATCAAAATACTGTTCTGACATCAGGCAGTGCAGGTGCAGACAT
TTAAGCCAATTGCTGCCGCCATTCTTTGACGTAGTCAATCAGGGCGCGGAGCTT
TGGTGCAATATTGCGACGCTGTGGGAAATACAGATAGAAGCCCGGAAATTGTG
```

-continued
```
GAAGAAAGTCATCAAGCAGCGATACAAGTTTACCGCTTTCAATATATGGCCTG

AAAGTTTCCTGAGTGGCAATTGTTATTCCTCCGCCGGCAAGAGCCAGCCTCAA

CATCAGACGCAGATCATTAGTCGTAATCTGCGGTTCAATCGCAAGGTCGAAAG

TTCTCCCGTTTTCTTCAAATGGCCAGCGATAAGGCGCAACCTCCGGGGACTGAC

GCCAGCCGATACACTTATGGGTATTTCCCCCGGAGGCGAGAAAGCACTCTCCA

CGCCCGGCCGCAAGGATCAGGACGACGGGGGCAGGCATGAATCCTCCTCCTG

ATGGAGACGTACAGAGGCGACTTCTGCCAGCACGGAGAGTGCCAGAGTATGC

GCATCCCGGGCTTTGGGGAATATCCCGACGGGTGCCCGGATTTGCGTTGTTTCC

TCCCTGGACCATCCCAGCTCGTGGAGCTTTTGCAGACGTAACGTGTGGGTTCGA

TAGCTGCCCAATGCGCCGAGATAAAAGGGTTTTGCTTCTCGCGCGGCCTGCAA

CACTGGCAGCTCCCGGTTGAGATCATGGCACAGCAAAATGACCGCCGTATCGG

TATCGATCTGAGCGCTGGCTGAGGCCGGAAAAAGATCGAAGATATGGCTGTCA

TAGCCTGTGGCTGCTGCAAGACTCGCGGTTGCCTGCGCCTCAAGAGAACGTCC

GTAAATCATCAGCCTGACGCATGGCCTGAACCCCACCTCAAAGCCATTGAGAT

TCCAGCCCGTCCGGGTTTGCGTGGGCAGGCACACCAGCGATTGTGCTTGCGGA

TCGTAGCGCAGCCCCACCGGTTTTCTCTGTTCCAGGCGGTTCAGCACGGCGAG

CAGAGGCTGTGCCGAGCGTAGggtacctcttaattaa
``` lower case corresponding to AscI, StuI and AvrII restriction sites
underlined lower cases homologous to sequence upstream of the CP4-6 locus (260955-261980, ecogene.org).
bold upper case corresponding to a TT02 transcriptional terminator sequence from the $7_1$ of E. coli rrnB gene (Orosz A, Boros I and Venetianer P. Eur. J. Biochem. 1991 Nov. 1; 201(3):653-9)
italic upper case sequence corresponding to a MCS containing BstZ17I, HindIII, ApaI, SmaI and BamHI restriction sites
upper case homologous to sequence downstream of the CP4-6 locus (296511-297581, ecogene.org)
underlined lower case corresponding to KpnI and PacI restriction sites. Second, primers Ome 1605-K7_Km_ampl_SmaI_BstZ17I_F (SEQ ID No 20) and Ome 1606-K7_Km_ampl_HindIII_R (SEQ ID No 21), were used to amplify the kanamycin cassette from plasmid pKD4 that was subsequently cloned between the BstZ17I and HindIII sites of the pMA-ΔCP4-6::TT02-MCS. The resulting plasmid was verified by DNA sequencing and called pMA-ΔCP4-6::TT02-MCS-Km.

```
Ome 1605-K7_Km_ampl_SmaI_BstZ17I_F
                                       (SEQ ID N°20)
TCCCCCGGGGTATACCATATGAATATCCTCCTTAG
``` with
underlined upper case sequence for BstZ17I and SmaI restriction sites and extrabases,
upper case sequence corresponding to site primer 1 of plasmid pKD4 (Datsenko, K. A. & Wanner, B. L., 2000, PNAS, 97: 6640-6645)

```
Ome 1606-K7_Km_ampl_HindIII_R
                                       (SEQ ID N°21)
GCCCAAGCTTTGTAGGCTGGAGCTGCTTCG
``` with
underlined upper case sequence for HindIII restriction site and extrabases,
upper case sequence corresponding to site primer 2 of plasmid pKD4 (Datsenko, K. A. & Wanner, B. L., 2000, PNAS, 97: 6640-6645)

To construct pMA-ΔCP4-6::TT02-TTadc-PlambdaR*(-35)-RBS01-thrA*1-cysE-PgapA-metA*11::Km the TTadc-PlambdaR*(-35)-RBS01-thrA*1-cysE-PgapA-metA*11 ApaI/BamHI digested fragment from pCL1920-TTadc-PlambdaR*(-35)-RBS01-thrA*1-cysE-PgapA-metA*11 described above was cloned into the ApaI and BamHI sites of pMA-ΔCP4-6::TT02-MCS-Km described above. The resulting plasmid was verified by DNA sequencing and called pMA-ΔCP4-6::TT02-TTadc-PlambdaR*(-35)-RBS01-thrA*1-cysE-PgapA-metA*11::Km I.5.2. Construction of Strain MG1655 metA*11 DCP4-6::TT02-TTadc-PlambdaR*(-35)-RBS01-thrA*1-cysE-PgapA-metA*11::Km (pKD46)

To replace the CP4-6 operon by the TT02-TTadc-PlambdaR*(-35)-RBS01-thrA*1-cysE-PgapA-metA*11::Km fragment plasmid pMA-ΔCP4-6::TT02-TTadc-PlambdaR*(-35)-RBS01-thrA*1-cysE-PgapA-metA*11::Km was digested by KpnI and AvrII and the remaining digested fragment ΔCP4-6::TT02-TTadc-PlambdaR*(-35)-RBS01-thrA*1-cysE-PgapA-metA*11::Km was introduced into the strain MG1655 metA*11 pKD46 according to Protocol 1.

Kanamycin resistant recombinants were selected and the presence of the ΔCP4-6::TT02-TTadc-PlambdaR*(-35)-RBS01-thrA*1-cysE-PgapA-metA*11::Km chromosomal modification was verified by PCR with primers Ome1775-DCP4-6_verif_F (SEQ ID No 22) and Ome1776-DCP4-6_verif_R (SEQ ID No 23) (Table 2) and by DNA sequencing. The resulting strain was called MG1655 metA*11 ΔCP4-6::TT02-TTadc-PlambdaR*(-35)-RBS01-thrA*1-cysE-PgapA-metA*11::Km (pKD46)

I.5.3. Transduction of ΔCP4-6::TT02-TTadc-PlambdaR*(-35)-RBS01-thrA*1-cysE-PgapA-metA*11::Km into Strain 4 and Removal of the Resistance cassette.

The ΔCP4-6::TT02-TTadc-PlambdaR*(-35)-RBS01-thrA*1-cysE-PgapA-metA*11::Km chromosomal modification was transduced into strain 4 (Table 1), described above, with a P1 phage lysate from strain MG1655 metA*11 pKD46 ΔCP4-6::TT02-TTadc-PlambdaR*(-35)-RBS01-thrA*1-cysE-PgapA-metA*11::Km described above, according to Protocol 2. Kanamycin resistant transductants were selected and the presence of the ΔCP4-6::TT02-TTadc-PlambdaR*(-35)-RBS01-thrA*1-cysE-PgapA-metA*11::Km chromosomal modification was verified by PCR with Ome1775-DCP4-6_verif_F (SEQ ID No 22) and Ome1776-DCP4-6_verif_R (SEQ ID No 23) (Table 2). The resulting strain was called MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS:: TTadc-CI857-PlambdaR*(-35)-thrA*1-cysE ΔpgaABCD:: TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11::Km.

Finally, the kanamycin resistance cassette of the above strain was removed by using Protocol 1. The loss of the kanamycin resistance cassette was verified by PCR by using primers Ome1775-DCP4-6_verif_F (SEQ ID No 22) and Ome1776-DCP4-6_verif_R (SEQ ID No 23) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 was called strain 5.

I.6. Construction of Strain 6

To insert the TT02-serA-serC region, which encodes an *E. coli* phosphoglycerate dehydrogenase and a phosphoserine aminotransferase, respectively, at the treBC locus, a two steps methods was used. First plasmid pMA-ΔtreBC::TT02-serA-serC:: Gt was constructed and second the ΔtreBC::TT02-serA-serC::Gt fragment that contains upstream and downstream regions homologous to the treBC locus was recombined into the chromosome according to Protocol 1.

I.6.1. Construction of plasmid pMA-ΔtreBC::TT02-serA-serC::Gt Plasmid pMA-ΔtreBC::TT02-serA-serC::Gt is derived from pMA-ΔtreBC::TT02-MCS::Gt described below, p34S-Gm (Dennis et Zyltra, AEM July 1998, p 2710-2715), and pUC18-serA-serC, which has been described in patent application PCT/FR2009/052520.

First plasmid pMA-ΔtreBC::TT02-MCS was been synthesized by GeneArt (www.geneart.com). The ΔtreBC::TT02-MCS fragment was cloned into the AscI and PacI sites of plasmid pMA from GeneArt and which contains the following sequence, identified as SEQ ID No 24:

```
ggcgcgccgGCAATCAAAATCCTGATGCAACGGCTGTATGACCAGGGGCATCGTAA

TATCAGTTATCTCGGCGTGCCGCACAGTGACGTGACAACCGGTAAGCGACGTC

ACGAAGCCTACCTGGCGTTCTGCAAAGCGCATAAACTGCATCCCGTTGCCGCC

CTGCCAGGGCTTGCTATGAAGCAAGGCTATGAGAACGTTGCAAAAGTGATTAC

GCCTGAAACTACCGCCTTACTGTGCGCAACCGACACGCTGGCACTTGGCgcaagta aatacctgcaagagcaacgcatcgacaccttgcaactggcgagcgtcggtaatacgccgttaa tgaaattcctccatccggagatcgtaaccgtagatcccggttacgccgaagctggacgccagg cggcttgccagttgatcgcgcaggtaaccgggcgcagcgaaccgcaacaaatcatcatcccc gccaccctgtcctgatcgtttcctgaacgataaaattgtgatctCATCAAATAAAACGA

AAGGCTCAGTCGAAAGACTGGGCCTTTCGTTTTATCTGTTGTATACAAGCTT

AATAAGGGCCCGGGCGGATCCGTCTGTCAGTATGTTGTTTTTGTTGATTTTTCAA

CCAGCAAATTCATTAAAAAATTTACATATCGCTGTAGCGCCCGTCATCCGTACG

CTCTGCTTTTTACTTTGAGCTACATCAAAAAAAGCTCAAACATCCTTGATGCAA

AGCACTATATATAGACTTTAAAATGCGTCCCAACCCAATATGTTGTATTAATCG

ACTATAATTGCTACTACAGCTCCCCACGAAAAAGGTGCGGCGTTGTGGATAAG

CGGATGGCGATTGCGGAAAGCACCGGAAAACGAAACGAAAAAACCGGAAAAC

GCCTTTCCCAATTTCTGTGGATAACCTGTTCTTAAAAATATGGAGCGATCATGA

CACCGCATGTGATGAAACGAGACGGCTGCAAAGTGCCGTTTAAATCAGAGCGC

ATCAAAGAAGCGATTCTGCGTGCAGCTAAAGCAGCGGAAGTCGATGATGCCG

ATTATTGCGCCACTGTTGCCGCGGTTGTCAGCGAGCAGATGCAGGGCCGCAAC

CAGGTGGATATCAATGAGATCCAGACCGCAGTTGAAAATCAGCTGttaattaa
``` lower cases corresponding to AscI restriction site
underlined upper cases homologous sequence upstream of the treBC locus (4460477-4461034).
bold upper cases corresponding to a TT02 transcriptional terminator sequence from the $T_1$ terminator of the *E. coli* rrnB gene (Orosz A, Boros I and Venetianer P. Eur. J. Biochem. 1991 Nov. 1; 201(3):653-9)

italic upper cases corresponding to a multiple cloning sites containing BstZ17I, HindIII, ApaI, SmaI and BamIII restriction sites upper cases homologous to sequence downstream of the treBC locus (4464294-4464787)

italic lower cases corresponding to PacI restriction site

To construct plasmid pMA-ΔtreBC::TT02-MCS::Gt, the FRT-Gt-FRT resistance cassette was amplified by PCR with primers BstZ17I-FRT-Gt-F (SEQ ID No 25) and HindIII-FRT-Gt-R (SEQ ID No 26) using p34S-Gm as template.

```
BstZ17I-FRT-Gt-F
                                         (SEQ ID N°25)
TCCCCCGGGGTATACTGTAGGCTGGAGCTGCTTCGAAGTTCCTATACTTT

CTAGAGAATAGGAACTTCGGAATAGGAACTTCATTTAGATGGGTACCGAG

CTCGAATTG
``` with
- underlined upper case sequence for SmaI and BstZ17I restriction sites and extrabases,
- bold upper case sequence corresponding to the FRT sequence (Datsenko, K. A. & Wanner, B. L., 2000, PNAS, 97: 6640-6645)
- upper case sequence homologous to sequence of the gentamycin gene located on p34S-Gm (Dennis et Zyltra, AEM July 1998, p 2710-2715).

```
HindIII-FRT-Gt-R
                                         (SEQ ID N°26)
CCCAAGCTTCATATGAATATCCTCCTTAGTTCCTATTCCGAAGTTCCTAT

TCTCTAGAAAGTATAGGAACTTCGGCGCGGATGGGTACCGAGCTCGAATT

G
``` with
- underlined upper case sequence for the HindIII restriction site and extrabases,
- bold upper case sequence corresponding to the FRT sequence (Datsenko, K. A. & Wanner, B. L., 2000, PNAS, 97: 6640-6645)
- upper case sequence homologous to the sequence of the gentamycin gene located on p34S-Gm (Dennis et Zyltra, AEM July 1998, p 2710-2715).

The FRT-Gt-FRT PCR product was then cloned between the BstZ17I and HindIII sites of pMA-ΔtreB::TT02-MCS. The resulting plasmid was verified by DNA sequencing and called pMA-ΔtreBC::TT02-MCS-Gt.

To construct the final plasmid pMA-ΔtreBC::TT02-serA-serC::Gt, pUC18-serA-serC was digested by HindIII and the serA-serC digested fragment was cloned into the pMA-ΔtreBC::TT02-MCS-Gt that had been linearized by HindIII. The resulting plasmid was verified by digestion and by DNA sequencing and was called pMA-ΔtreBC::TT02-serA-serC::Gt I.6.2. Construction of Strain MG1655 metA*11 pKD46 ΔtreBC::TT02-serA-serC::Gt To replace the treBC gene by the TT02-serA-serC::Gt fragment, pMA-ΔtreBC::TT02-serA-serC::Gt was digested by ApaI and SalI and the remaining digested fragment ΔtreBC::TT02-serA-serC::Gt was introduced into the strain MG1655 metA*11 pKD46 according to Protocol 1.

Gentamycin resistant recombinants were selected and the presence of the ΔtreBC::TT02-serA-serC::Gt fragment was verified by PCR with primers Ome 1595-DtreB_verif_F (SEQ ID No 27) and Ome 1596-DtreB_verif_R (SEQ ID No 28) (Table 2) and by DNA sequencing. The resulting strain was called MG1655 metA*11 pKD46 ΔtreBC::TT02-serA-serC::Gt.

I.6.3. Transduction of ΔtreBC::TT02-serA-serC::Gt into strain 5

The ΔtreBC::TT02-serA-serC::Gt chromosomal modification was then transduced into strain 5 (Table 1) with a P1 phage lysate from strain MG1655 metA*11 pKD46 ΔtreBC::TT02-serA-serC::Gt described above, according to Protocol 2.

Gentamycin resistant transductants were selected and the presence of the DtreBC::TT02-serA-serC::Gt chromosomal modification was verified by PCR with Ome 1595-DtreB_verif_F (SEQ ID No 27) and Ome 1596-DtreB_verif_R (SEQ ID No 28) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔtreBC::TT02-serA-serC::Gt was called strain 6.

I.7. Construction of Strain 7 by Transduction of Ptrc36-metF::Km into Strain 6

Overexpression of the metF gene from artificial promoter integrated at the metF locus into the chromosome, strain MG1655 metA*11 ΔmetJ Ptrc36-metF::Km, has been described in patent application WO 2007/077041.

The Ptrc36-metF::Km promoter construct was transduced into strain 6 (Table 1) with a P1 phage lysate from strain MG1655 metA*11 ΔmetJ Ptrc36-metF::Km according to Protocol 2.

Kanamycin resistant transductants were selected and the presence of the Ptrc36-metF::Km promoter construct was verified by PCR with primers Ome0726-PtrcmetF-F (SEQ ID No 29) and Ome0727-PtrcmetF-R (SEQ ID No 30) (Table 2). The resulting strain MG1655 metA*11 Ptrc-metH PtrcF-cysPUWAM PtrcF-cysJIH Ptrc09-gcvTHP Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔtreBC::TT02-serA-serC::Gt Ptrc36-metF::Km was called strain 7.

II. Example 2

Construction of Strain 9, MG1655 metA*11 Ptrc-metH PtrcF-cysPUWAM PtrcF-cysJIH Ptrc09-gcvTHP Ptrc36-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 DtreBC::TT02-serA-serC::Gt Ptrc01-pntAB::Cm ΔudhA::Km II.1. Construction of Strain 8

II.1.1. Construction of MG1655 metA*11 ΔmetJ Ptrc36-metF by Removal of the kanamycine Resistance Cassette The kanamycin resistance of the strain MG1655 metA*11 ΔmetJ Ptrc36-metF::Km, described in patent application WO2007/077041, was removed according to Protocol 1. Loss of the kanamycin resistant cassette was verified by PCR by using the primers Ome0726-PtrcmetF-F (SEQ ID No 29) and Ome0727-PtrcmetF-R(SEQ ID No 30) (Table 2). The resulting strain was called MG1655 metA*11 ΔmetJ Ptrc36-metF.

II.1.2. Construction of MG1655 metA*11 ΔmetJ Ptrc36-metF ΔudhA::Km pKD46 To delete the udhA gene in strain MG1655 metA*11 ΔmetJ Ptrc36-metF, Protocol 1 has been used except that primers Ome0032-DUdhAF (SEQ ID No 31) and Ome0034-DUdhAR (SEQ ID No 32) were used to amplify the kanamycin resistance cassette from plasmid pKD4.

Kanamycin resistant recombinants were selected. The insertion of the resistance cassette was verified by PCR with primers Oag0055-udhAF2 (SEQ ID No 33) and Oag0056-udhAR2 (SEQ ID No 34) (Table 2) and by DNA sequencing. The resulting strain was called MG1655 metA*11 ΔmetJ Ptrc36-metF ΔudhA::Km pKD46.

Ome0032-DUdhAF
(SEQ ID N°31)
GGTGCGCGCGTCGCAGTTATCGAGCGTTATCAAAATGTTGGCGGCGGTTG

CACCCACTGGGGCACCATCCCGTCGAAAGC<u>CATATGAATATCCTCCTTAG</u> with:
- upper case sequence homologous to sequence upstream of the udhA gene (4158729-4158650, reference sequence on the website ecogene.org)
- underlined upper case sequence corresponding to the primer site 1 of plasmid pKD4 (Datsenko, K. A. & Wanner, B. L., 2000, PNAS, 97: 6640-6645)

Ome0034-DUdhAR
(SEQ ID N°32)
CCCAGAATCTCTTTTGTTTCCCGATGGAACAAAATTTTCAGCGTGCCCAC

GTTCATGCCGACGATTTGTGCGCGTGCCAGT<u>GTAGGCTGGAGCTGCTTCG</u> with
- upper case sequence homologous to sequence downstream of the udhA gene (4157588-4157667, reference sequence on the website ecogene.org)
- underlined upper case sequence corresponding to the primer site 2 of plasmid pKD4 (Datsenko, K. A. & Wanner, B. L., 2000, PNAS, 97: 6640-6645)

II.1.3. Co-transduction of Ptrc36-metF ΔudhA::Km into Strain 6

The genes udhA and metF are close on the *E. coli* chromosome, 89.61 min and 89.03 min respectively and since phage P1 can package 2 min of the *E. coli* chromosome, the genes udhA and metF are co-transducibles. Thereby, the Ptrc36-metF promoter modification and ΔudhA::Km deletion described above, were co-transduced into strain 6 (Table 1) by using a P1 phage lysate from the strain MG1655 metA*11 ΔmetJ Ptrc36-metF ΔudhA::Km pKD46, described above, according to Protocol 2.

Kanamycin resistant transductants were selected. The presence of the Ptrc36-metF promoter modification was verified by PCR with primers Ome0726-PtrcmetF-F (SEQ ID No 29) and Ome0727-PtrcmetF-R (SEQ ID No 30) followed by DNA sequencing. The presence of the DudhA::Km deletion was verified by PCR with primers Oag0055-udhAF2 (SEQ ID No 33) and Oag0056-udhAR2 (SEQ ID No 34) (Table 2). The resulting strain MG1655 metA*11 Ptrc-metH PtrcF-cysPUWAM PtrcF-cysJIH Ptrc09-gcvTHP Ptrc36-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔtreBC::TT02-serA-serC::Gt ΔudhA::Km was called strain 8.

II.2. Construction of Strain 9

II.2.1. Construction of Strain MG1655 metA*11 pKD46 Ptrc01-pntAB::Cm

To increase the expression level of pyridine nucleotide transhydrogenase alpha and beta subunits, PntA and PntB, a constitutive artificial trc01 promoter was added upstream of the pntAB operon into the strain MG1655 metA*11 pKD46 according to Protocol 1, except that primers Ome1149-Ptrc-pntAF (SEQ ID No 35) and Ome 1150-Ptrc-pntAR (SEQ ID No 36) were used to amplify the chloramphenicol resistance cassette from plasmid pKD3. Chloramphenicol resistant recombinants were selected. The presence of the artificial promoter Ptrc01 and the insertion of the resistance cassette were verified by PCR with primers Ome1151-pntAF (SEQ ID No 37) and Ome1152-pntAR (SEQ ID No 38) (Table 2) and by DNA sequencing. The resulting strain was called MG1655 metA*11 pKD46 Ptrc01-pntAB::Cm.

Ome 1149-Ptrc-pntAF
(SEQ ID N°35)
GCTCGTACATGAGCAGCTTGTGTGGCTCCTGACACAGGCAAACCATCAT CAATAAAACCGAT<u>TCACACTGGCTCACCTTCGGGTGGGCCTTTCTGC</u>CA

*TATGAATATCCTCCTTAG* with
- upper case sequence homologous to sequence upstream of the pntA gene (1676002-1675941 reference sequence on the website ecogene.org)
- underlined upper case sequence for T7Te transcriptional terminator sequence from phage T7 (Harrington K. J., Laughlin R. B. and Liang S. Proc Natl Acad Sci USA. 2001 Apr. 24; 98(9):5019-24.),
- italic upper case sequence corresponding to the primer site 1 of plasmid pKD3 (Datsenko, K. A. & Wanner, B. L., 2000, PNAS, 97: 6640-6645)

Ome 1150-Ptrc-pntAR
(SEQ ID N°36)
GCTGCAACACGGGTTTCATTGGTTAACCGTTCTCTTGGTATGCCAATTCG CATGATATTCCCTTCC<u>TTCCACACATTATACGAGCCGGATGATTAATTGT</u>

<u>CAACAGCTC</u>*TGTAGGCTGGAGCTGCTTCG* with
- upper case sequence homologous to sequence upstream of the pntA gene (1675875-1675940, reference sequence on the website ecogene.org)
- underlined upper case sequence for the trc promoter sequence
- Italic upper case sequence corresponding to the primer site 2 of plasmid pKD3 (Datsenko, K. A. & Wanner, B. L., 2000, PNAS, 97: 6640-6645)

II.2.2. Transduction of Ptrc01-pntAB::Cm into Strain 8

The Ptrc01-pntAB::Cm promoter modification was transduced into strain 8 (Table 1) according to Protocol 2 by using a P1 phage lysate from strain MG1655 metA*11 pKD46 Ptrc01-pntAB::Cm described above.

Chloramphenicol resistant transductants were selected and the presence of the Ptrc01-pntAB::Cm chromosomal modification was verified by PCR with Ome1151-pntAF (SEQ ID No 37) and Ome1152-pntAR (SEQ ID No 38) (Table 2). The resulting strain MG1655 metA*11 Ptrc-metH PtrcF-cysPU-WAM PtrcF-cysJIH Ptrc09-gcvTHP Ptrc36-metF Ptrc07-serB ΔmetJ ΔpykF 4pykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔtreBC::TT02-serA-serC::GtPtrc01-pntAB::Cm ΔudhA::Km was called strain 9.

III. Example 3

Construction of Strain 10, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC III.1. Construction of plasmid pUC18-ΔwcaM::TT02-TTadc-PlambdaR*(-35)-RBS01-thrA*1-cysE-PgapA-metA*11::Cm Plasmid pUC18-ΔwcaM::TT02-TTadc-PlambdaR*(-35)-RBS01-thrA*1-cysE-PgapA-metA*11::Cm is derived from plasmid pCL1920-TTadc-PlambdaR*(-35)-RBS01-thrA*1-cysE-PgapA-metA*11 described above and plasmid pUC18-ΔwcaM::TT02-MCS::Cm described below.

III.1.1. Construction of Plasmid pUC18-ΔwcaM::TT02-MCS::Cm

To construct the DwcaM::TT02-MCS::Cm fragment, overlapping PCR between the upstream region of wcaM (up-wcaM), the TT02 transcriptional terminator, the multiple cloning site (MCS) and the downstream region of wcaM (downwcaM) was done and the chloramphenicol cassette (Cm) was amplified and cloned subsequently.

First, the fragment upwcaM-TT02 was amplified from E. coli MG1655 genomic DNA using primers Ome 1703-DwcaM-HpaI-EcoRI-F (SEQ ID No 39) and Ome 1704-DwcaM-TT02-BstZ17I-R (SEQ ID No 40) by PCR. Then, the TT02-MCS-downwcaM fragment was amplified from E. coli MG1655 genomic DNA using primers Ome 1705-DwcaM-MCS-BstZ17I-F (SEQ ID No 41) and Ome 1706-DwcaM-EcoRI-R (SEQ ID No 42) by PCR. Primers Ome 1704-DwcaM-TT02-BstZ17I-R (SEQ ID No 40) and Ome 1705-DwcaM-MCS-BstZ17I-F (SEQ ID No 41) have been designed to overlap through a 36 nucleotides-long region. Finally, the upwcaM-TT02-MCS-downwcaM fragment was amplified by mixing the upwcaM-TT02 and the TT02-MCS-downwcaM amplicons and using primers Ome 1703-DwcaM-HpaI-EcoRI-F (SEQ ID No 39) and Ome 1706-DwcaM-EcoRI-R (SEQ ID No 42). The resulting fusion PCR product was digested by HpaI and cloned between the HindIII and EcoRI sites of plasmid pUC18 that had been treated by Large (Klenow) Fragment of E. coli DNA Polymerase I. The resulting plasmid was verified by DNA sequencing and called pUC18-ΔwcaM::TT02-MCS.

Ome 1703-DwcaM-HpaI-EcoRI-F
(SEQ ID N°39)
CGTAGTTAACGAATTCCTGCGCCACCGAGCCAGCCAGACCTTGCGC with
underlined upper case sequence for HpaI and EcoRI restriction sites and extrabases,
upper case sequence homologous to sequence downstream of the wcaM gene (2114909-2114938, reference sequence on the website ecogene.org)

Ome 1704-DwcaM-TT02-BstZ17I-R
(SEQ ID N°40)
GCTTGTATACAACAGATAAAACGAAAGGCCCAGTCTTTCGACTGAGCCTT
TCGTTTTATTTGATGGCGTTCTCCTCTATAAAGCCTGCAGCAAGC with
bold upper case sequence for the BstZ17I restriction site and extrabases,
underlined upper case sequence corresponding to the transcriptional terminator $T_1$ of E. coli rrnB (Orosz A, Boros I and Venetianer P. Eur. J. Biochem. 1991 Nov. 1; 201(3):653-9)
upper case sequence homologous to sequence downstream of the wcaM gene (2113921-2113950, reference sequence on the website ecogene.org).

Ome 1705 (DwcaM-MCS-BstZ17I-F)
(SEQ ID N°41)
AGACTGGGCCTTTCGTTTTATCTGTTGTATACAAGCTTAATTAAGGGCCC
GGGCGGATCCATTTGCGACCATTCCTGGAAAAATGGAGTC with
bold upper case sequence complementary to the 3' end sequence of the transcriptional terminator $T_1$ of E. coli rrnB (Orosz A, Boros I and Venetianer P. Eur. J. Biochem. 1991 Nov. 1; 201(3):653-9),
underlined upper case sequence containing a multiple cloning site: BstZ17I, HindIII, PacI, ApaI, BamHI,
upper case sequence homologous to sequence upstream of the wcaM gene (2112496-2112525, reference sequence on the website ecogene.org)

Ome 1706 (DwcaM-EcoRI-R)
(SEQ ID N°42)
CGTAGTTAACGAATTCCGCCCCTTCTTTCAGGTTGCGTAGGCCATAC with
bold upper case sequence for HpaI and EcoRI restriction sites and extrabases,
upper case sequence homologous to sequence upstream of the wcaM gene (2111497-2111527, reference sequence on the website ecogene.org)

Finally, primers Ome 1603-K7_Cm_ampl_SmaI_BstZ17I_F (SEQ ID No 9) and Ome 1604-K7_Cm_ampl_HindIII_R (SEQ ID No 10), described above, were used to amplify the chloramphenicol cassette from plasmid pKD3. The cassette was then cloned between the BstZ17I and HindIII sites of plasmid pUC18-ΔwcaM::TT02-MCS. The resulting plasmid was verified by DNA sequencing and called pUC18-ΔwcaM::TT02-MCS-Cm.

III.1.2. Construction of Plasmid pUC18-ΔwcaM::TT02-TTadc-PlambdaR*(-35)-RBS01-thrA*1-cysE-PgapA-metA*11::Cm To construct pUC18-ΔwcaM::TT02-TTadc-PlambdaR*(-35)-RBS01-thrA*1-cysE-PgapA-metA*11::Cm, the TTadc-PlambdaR*(-35)-RBS01-thrA*1-cysE-PgapA-metA*11 ApaI/BamHI digested fragment from pCL1920-TTadc-PlambdaR*(-35)-RBS01-thrA*1-cysE-PgapA-metA*11 described above was cloned between the ApaI and BamHI sites of pUC18-ΔwcaM::TT02-MCS-Cm described above. The obtained plasmid was verified by DNA sequencing and called pUC18-ΔwcaM::TT02-TTadc-PlambdaR*(-35)-RBS01-thrA*1-cysE-PgapA-metA*11::Cm III.2. Construction of Strain MG1655 metA*11 ΔwcaM::TT02-TTadc-PlambdaR*(-35)-RBS01-thrA*1-cysE-PgapA-metA*11::Cm pKD46

To replace the wcaM gene by the TT02-TTadc-PlambdaR*(-35)-RBS01-thrA*1-cysE-PgapA-metA*11::Cm region plasmid pUC18-ΔwcaM::TT02-TTadc-PlambdaR*(-35)-RBS01-thrA*1-cysE-PgapA-metA*11::Cm was digested by BspHI and the remaining digested fragment ΔwcaM::TT02-TTadc-PlambdaR*(-35)-RBS01-thrA*1-cysE-PgapA-metA*11::Cm was introduced into strain MG1655 metA*11 pKD46 according to Protocol 1.

Chloramphenicol resistant recombinants were selected and the presence of the ΔwcaM::TT02-TTadc-PlambdaR*(-35)-RBS01-thrA*1-cysE-PgapA-metA*11::Cm chromosomal modification was verified by PCR with primers Ome1707-DwcaM_verif_F (SEQ ID No 43) and Ome1708-DwcaM_verif_R (SEQ ID No 44) (Table 2) and by DNA sequencing. The verified and selected strain was called MG1655 metA*11 ΔwcaM::TT02-TTadc-PlambdaR*(-35)-RBS01-thrA*1-cysE-PgapA-metA*11::Cm (pKD46)

III.3. Transduction of DwcaM::TT02-TTadc-PlambdaR*(-35)-RBS01-thrA*1-cysE-PgapA-metA*11::Cm into Strain 6 and Removal of the resistance Cassette.

The ΔwcaM::TT02-TTadc-PlambdaR*(-35)-RBS01-thrA*1-cysE-PgapA-metA*11::Cm chromosomal modification was transduced into the strain 6 (Table 1) described above with a P1 phage lysate from strain MG1655 metA*11 pKD46 ΔwcaM::TT02-TTadc-PlambdaR*(-35)-RBS01-thrA*1-cysE-PgapA-metA*11::Cm described above, according to Protocol 2.

Chloramphenicol resistant transductants were selected and the presence of the ΔwcaM::TT02-TTadc-PlambdaR*(-35)-RBS01-thrA*1-cysE-PgapA-metA*11::Cm chromosomal modification was verified by PCR with Ome1707-DwcaM_verif_F (SEQ ID No 43) and Ome1708-DwcaM_verif_R (SEQ ID No 44) (Table 2). The resulting strain was called MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔtreBC::TT02-serA-serC::Gt ΔwcaM::TT02-TTadc-PlambdaR*(-35)-RBS01-thrA*1-cysE-PgapA-metA*11:: Cm.

The gentamycin and chloramphenicol cassettes of the above strain were then removed according to Protocol 1. The loss of the gentamycin and chloramphenicol resistance cassettes was verified by PCR by using primers Ome 1595-DtreB_verif_F (SEQ ID No 27) and Ome 1596-DtreB_verif_R (SEQ ID No 28) and primers Ome1707-DwcaM_verif_F (SEQ ID No 43) and Ome1708-DwcaM_verif_R (SEQ ID No 44) (Table 2) respectively. The resulting strain MG1655 metA*11 Ptrc-metHPtrcF-cysPUWAMPtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC was called strain 10.

IV. Example 4

Construction of Strain 12, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC Ptrc01-pntAB:: Cm pCL1920-PgapA-pycre-TT07

IV.1. Construction of Strain 11 by Transduction of Ptrc01-pntAB::Cm into Strain 10

The Ptrc01-pntAB::Cm promoter modification described above was transduced into strain 10 (Table 1) according to Protocol 2 by using a P1 phage lysate from strain MG1655 metA*11 pKD46 Ptrc01-pntAB::Cm described above.

Chloramphenicol resistant transductants were selected and the presence of the Ptrc01-pntAB::Cm chromosomal modification was verified by PCR with primers Ome1151-pntAF (SEQ ID No 37) and Ome1152-pntAR (SEQ ID No 38) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serCPtrc01-pntAB::Cm was called strain 11.

IV.2. Construction of pCL1920-PgapA-pycRe-TT07 and Introduction into Strain 11

In order to overexpress the pyruvate carboxylase gene of Rhizobium etli, plasmid pCL1920-PgapA-pycRe-TT07 was constructed, which is derived from plasmid pCL1920 (Lerner & Inouye, 1990, NAR 18, 15 p 4631).

To construct the PgapA-pycRe-TT07 insert, overlapping PCR between the gapA promoter, its Ribosome Binding Site (RBS) and the pycRe gene of Rhizobium etli has been used.

First, the gapA promoter and RBS region (corresponding to the -156 to -1 region upstream of the gapA start codon) was amplified from E. coli MG1655 genomic DNA by PCR using primers PgapA-SalI-F (SEQ ID No 45) and PgapA-pycRe-R (SEQ ID No 46). Then, the pycRe gene was amplified from Rhizobium etli CFN 42 genomic DNA using primers PgapA-pycRe F (SEQ ID No 47) and pycRe-TT07-SmaI-R (SEQ ID No 48). Primers PgapA-pycRe-R (SEQ ID No 46) and PgapA-pycRe F (SEQ ID No 47) have been designed to overlap through a 42 nucleotides-long region. Finally, the PgapA-RBSgapA-pycRe-TT07 fragment was amplified by mixing the gapA promoter-RBS and the pycRe amplicons using primers PgapA-SalI-F (SEQ ID No 45) and pycRe-TT07-SmaI-R (SEQ ID No 48). The resulting fusion PCR product was cloned between the SalI and SmaI sites of plasmid pCL1920. The resulting plasmid was verified by DNA sequencing and called pCL1920-PgapA-pycRe-TT07.

PgapA-SalI-F (SEQ ID N°45)
<u>ACGCGTCGACGGTATCGATAAGCTTCGTTTAAA</u>CAAGCCCAAAGGAAGAG TGA

- underlined upper case sequence for SalI, ClaI, HindIII and PmeI restriction site and extrabases,
- bold upper case sequence homologous to the gapA promoter sequence (1860640-1860658, reference sequence on the website ecogene.org)

PgapA-pycRe-R (SEQ ID N°46)
GTATCTTGGATATGGGCATATGTTCCACCAGCTATTTGTTAG with

- bold upper case sequence homologous to the promoter of gapA gene (1860772-1860791, reference sequence on the website ecogene.org)
- upper case sequence homologous to pycRe gene, except that the GTG start codon of pycRe gene was replaced by ATG (4236889-4236906, reference sequence on the website www.ncbi.nlm.nih.gov).

PgapA-pycRe F (SEQ ID N°47)
CTAACAAATAGCTGGTGGAACATATGCCCATATCCAAGATAC with

- bold upper case sequence homologous to the promoter of gapA gene (1860772-1860791, reference sequence on the website ecogene.org)
- upper case sequence homologous to the pycRe gene, except that the GTG start codon of pycRe gene was replaced by an ATG (4236889-4236906, reference sequence on the website www.ncbi.nlm.nih.gov).

pycRe-TT07-SmaI-R (SEQ ID N°48)
<u>TCCCCCCGGGGATCCGAATTCGCAGAAAGGCCCACCCGAAGGTGAGCCAG</u>
*CTCGAGGG*CAAGGACGGGCGAACGAAACCTTTCGTGCCGTTCGCTCATCC GCCGTAAACCGCCAG with

- underlined upper case sequence for a SmaI, BamHI and EcoRI restriction sites and extrabases,
- upper case sequence corresponding to T7Te transcriptional terminator sequence from T7 phage (Harrington K. J., Laughlin R. B. and Liang S. Proc Natl Acad Sci USA. 2001 Apr. 24; 98(9):5019-24.),
- italic upper case sequence for XhoI restriction site and extrabases,
- bold upper case sequence homologous to sequence downstream of the pycRe gene (4240332-4240388, reference sequence on the website www.ncbi.nlm.nih.gov)

Then, the pCL1920-PgapA-pycRe-TT07 was introduced by electroporation into strain 11 (Table 1). The presence of plasmid pCL1920-PgapA-pycRe-TT07 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC Ptrc01-pntAB::Cm pCL1920-PgapA-pycRe-TT07 was called strain 12.

V. Example 5

Construction of Strain 13, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC Ptrc01-pntAB::Cm ΔudhA::Km The ΔudhA::Km deletion described previously was transduced into strain 11 (Table 1) by using a P1 phage lysate from the strain MG1655 metA*11 ΔmetJ Ptrc36-metF ΔudhA::Km pKD46 described above according to Protocol 2

Kanamycin resistant transductants were selected. The presence of the Ptrc36-ARNmst17-metF promoter modification was verified by PCR with primers Ome0726-PtrcmetF-F (SEQ ID No 29) and Ome0727-PtrcmetF-R (SEQ ID No 30) followed by DNA sequencing and the presence of the ΔudhA::Km deletion was verified by PCR with primers Oag0055-udhAF2 (SEQ ID No 33) and Oag0056-udhAR2 (SEQ ID No 34) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serCPtrc01-pntAB::Cm ΔudhA::Km was called strain 13.

VI. Example 6

Construction of Strain 14 MG1655 metA*11 Ptrc-metH PtrcF-cysPUWAM PtrcF-cysJIH Ptrc09-gcvTHP Ptrc36-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6:: TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC Ptrc01-pntAB::Cm ΔudhA::Km The genes udhA and metF are close on the *E. coli* chromosome, 89.61 min and 89.03 min respectively and since phage P1 can package 2 min of the *E. coli* chromosome, the genes udhA and metF are co-transducibles. Thereby, the Ptrc36-metF promoter modification and ΔudhA::Km deletion described above, were co-transduced into strain 11 (Table 1) by using a P1 phage lysate from the strain MG1655 metA*11 ΔmetJ Ptrc36-metF ΔudhA::Km pKD46, described above, according to Protocol 2.

Kanamycin resistant transductants were selected. The presence of the Ptrc36-metF promoter modification was verified by PCR with primers Ome0726-PtrcmetF-F (SEQ ID No 29) and Ome0727-PtrcmetF-R (SEQ ID No 30) followed by DNA sequencing. The presence of the ΔudhA::Km deletion was verified by PCR with primers Oag0055-udhAF2 (SEQ ID No 33) and Oag0056-udhAR2 (SEQ ID No 34) (Table 2). The resulting strain MG1655 metA*11 Ptrc-metH PtrcF-cysPUWAM PtrcF-cysJIH Ptrc09-gcvTHP Ptrc36-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6:: TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC Ptrc01-pntAB::Cm Δ udhA::Km was called strain 14.

VII. Example 7

Construction of Strain 15, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC Ptrc01-pntAB::Cm ΔudhA::Km pCL1920-PgapA-pycre-TT07

The pCL1920-PgapA-pycRe-TT07, described previously, was introduced by electroporation into strain 13 (Table 1). The presence of plasmid pCL1920-PgapA-pycRe-TT07 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA:: TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC Ptrc01-pntAB::Cm ΔudhA::Km pCL1920-PgapA-pycre-TT07 was called strain 15.

VIII. Example 8

Construction of Strain 18, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC Ptrc30-pntAB::Cm ΔudhA pCL1920-PgapA-pycRe-TT07

VIII.1. Construction of Strain 16 by Removal of the Resistance Cassettes of Strain 13

The kanamycin and chloramphenicol resistance cassettes of the strain 13, described above, were removed according to Protocol 1. The loss of the kanamycin and chloramphenicol resistant cassettes were verified by PCR by using the primers with primers Oag0055-udhAF2 (SEQ ID No 33), Oag0056-udhAR2 (SEQ ID No 34), Ome1151-pntAF (SEQ ID No 37) and Ome1152-pntAR (SEQ ID No 38) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS:: TTadc-C1857-PlambdaR*(-35)-thrA*1-cysE ΔpgaABCD:: TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC Ptrc01-pntAB ΔudhA pCL1920-PgapA-pycRe-TT07 was called strain 16.

VIII.2. Construction of Strain MG1655 metA*11 pKD46 Ptrc30-pntAB::Cm

To increase the expression level of pyridine nucleotide transhydrogenase alpha and beta subunits, PntA and PntB, a constitutive artificial trc30 promoter was added upstream of pntA-pntB operon into the strain MG1655 metA*11 pKD46 according to Protocol 1, except that primers Ome2104 Ptrc30-pntAR (SEQ ID No 49) and Ome 1150-Ptrc-pntAF (SEQ ID No 36) were used to amplify the chloramphenicol resistance cassette from pKD3 plasmid.

Chloramphenicol resistant recombinants were selected. The presence of the artificial promoter trc30 and the insertion of the resistance cassette were verified by PCR with primers Ome1151-pntAF (SEQ ID No 37) and Ome1152-pntAR (SEQ ID No 38) (Table 2) and by DNA sequencing. The verified and selected strain was called MG1655 metA*11 pKD46Ptr30-pntAB::Cm.

Ome2104 Ptrc30-pntA R
(SEQ ID N°49)
GCTGCAACACGGGTTTCATTGGTTAACCGTTCTCTTGGTATGCCAATTCG CATGATATTCCCTTCC<u>TTCCACACAGTATACGAGCCGGATGATTAATCGT</u>

<u>CAACAGCTC</u>*TGTAGGCTGGAGCTGCTTCG* with
- upper case sequence homologous to sequence upstream the pntA gene (1675875-1675940, reference sequence on the website ecogene.org)
- underlined upper case sequence for the trc30 promoter sequence
- italic upper case sequence corresponding to the primer site 2 of pKD3 plasmid (Datsenko, K. A. & Wanner, B. L., 2000, PNAS, 97: 6640-6645)

VIII.3. Construction of Strain 17 by Transduction of Ptrc30-pntAB::Cm into Strain 16

The Ptrc30-pntAB::Cm promoter modification was transduced into the strain 16 (Table 1) by using a P1 phage lysate from the strain MG1655 metA*11 pKD46 Ptrc30-pntAB::Cm described above according to Protocol 2.

Chloramphenicol resistant transductants were selected and the presence of the Ptrc30-pntAB::Cm chromosomal modification was verified by PCR with Ome1151-pntAF (SEQ ID No 37) and Ome1152-pntAR (SEQ ID No 38) (Table 2). The verified and selected strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serCPtrc30-pntAB::Cm ΔudhA was called strain 17.

VIII.4. Construction of Strain 18 by Introduction of pCL1920-PgapA-pycre-TT07 into Strain 17

The pCL1920-PgapA-pycRe-TT07, described previously, was introduced by electroporation into strain 17 (Table 1). The presence of plasmid pCL1920-PgapA-pycRe-TT07 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC Ptrc30-pntAB::Cm ΔudhA pCL1920-PgapA-pycre-TT07 was called strain 18.

IX. Example 9

Construction of Strain 20, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC Ptrc97-pntAB::Cm ΔudhA pCL1920-PgapA-pycRe-TT07

IX.1. Construction of Strain MG1655 metA*11 pKD46 Ptrc97-pntAB::Cm

To increase the expression level of pyridine nucleotide transhydrogenase alpha and beta subunits, PntA and PntB, a constitutive artificial trc97 promoter was added upstream of pntA-pntB operon into the strain MG1655 metA*11 pKD46 according to Protocol 1, except that primers Ome2105 Ptrc97-pntAR (SEQ ID No 50) and Ome 1150-Ptrc-pntAF (SEQ ID No 36) were used to amplify the chloramphenicol resistance cassette from pKD3 plasmid.

Chloramphenicol resistant recombinants were selected. The presence of the artificial promoter trc97 and the insertion of the resistance cassette were verified by PCR with primers Ome1151-pntAF (SEQ ID No 37) and Ome1152-pntAR (SEQ ID No 38) (Table 2) and by DNA sequencing. The verified and selected strain was called MG1655 metA*11 pKD46Ptr97-pntAB::Cm.

Ome 2105 Ptrc97-pntAR
(SEQ ID N°50)
GCTGCAACACGGGTTTCATTGGTTAACCGTTCTCTTGGTATGCCAATTCG CATGATATTCCCTTCC<u>TTCCACACATTTTACGAGCCGGATGATTAATAGC</u>

<u>CAACAGCTC</u>*TGTAGGCTGGAGCTGCTTCG* with
- upper case sequence homologous to sequence upstream the pntA gene (1675875-1675940, reference sequence on the website ecogene.org)
- underlined upper case sequence for the trc97 promoter sequence
- Italic upper case sequence corresponding to the primer site 2 of pKD3 plasmid (Datsenko, K. A. & Wanner, B. L., 2000, PNAS, 97: 6640-6645)

IX2. Construction of Strain 19 by Transduction of Ptrc97-pntAB::Cm into Strain 16

The Ptrc97-pntAB::Cm promoter modification was transduced into the strain 16 (Table 1) by using a P1 phage lysate from the strain MG1655 metA*11 pKD46 Ptrc97-pntAB::Cm described above according to Protocol 2.

Chloramphenicol resistant transductants were selected and the presence of the Ptrc97-pntAB::Cm chromosomal modification was verified by PCR with Ome1151-pntAF (SEQ ID No 37) and Ome1152-pntAR (SEQ ID No 38) (Table 2). The verified and selected strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01- thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC::Gt Ptrc97-pntAB::Cm ΔudhA was called strain 19.

IX.3. Construction of Strain 20 by Introduction of pCL1920-PgapA-pycre-TT07 into Strain 19

The pCL1920-PgapA-pycRe-TT07, described previously, was introduced by electroporation into strain 19 (Table 1). The presence of plasmid pCL1920-PgapA-pycRe-TT07 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC Ptrc97-pntAB::Cm ΔudhA pCL1920-PgapA-pycre-TT07 was called strain 20.

X. Example 10

Construction of Strain 22, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC Ptrc55-pntAB::Cm ΔudhA pCL1920-PgapA-pycRe-TT07

X.1. Construction of Strain MG1655 metA*11 pKD46 Ptrc55-pntAB::Cm

To increase the expression level of pyridine nucleotide transhydrogenase alpha and beta subunits, PntA and PntB, a constitutive artificial trc55 promoter was added upstream of pntA-pntB operon into the strain MG1655 metA*11 pKD46 according to Protocol 1, except that primers Oag 0699-Ptrc55-pntAB R (SEQ ID No 51) and Ome 1150-Ptrc-pntAF (SEQ ID No 36) were used to amplify the chloramphenicol resistance cassette from pKD3 plasmid.

Chloramphenicol resistant recombinants were selected. The presence of the artificial promoter trc55 and the insertion of the resistance cassette were verified by PCR with primers Ome1151-pntAF (SEQ ID No 37) and Ome1152-pntAR (SEQ ID No 38) (Table 2) and by DNA sequencing. The verified and selected strain was called MG1655 metA*11 pKD46Ptr55-pntAB::Cm.

```
Oag 0699-Ptrc55-pntAB R
                                          (SEQ ID N°51)
GCTGCAACACGGGTTTCATTGGTTAACCGTTCTCTTGGTATGCCAATTCG

CATGATATTCCCTTCCTTCCACACACTATACGAGCCGGATGATTAATGGT

CAACAGCTCTGTAGGCTGGAGCTGCTTCG
``` with
upper case sequence homologous to sequence upstream the pntA gene (1675875-1675940, reference sequence on the website ecogene.org)
underlined upper case sequence for the trc55 promoter sequence
italic upper case sequence corresponding to the primer site 2 of pKD3 plasmid (Datsenko, K. A. & Wanner, B. L., 2000, PNAS, 97: 6640-6645)

X.2. Transduction of Ptrc55-pntAB::Cm into Strain 16

The Ptrc55-pntAB::Cm promoter modification was transduced into the strain 16 (Table 1) by using a P1 phage lysate from the strain MG1655 metA*11 pKD46 Ptrc55-pntAB::Cm described above according to Protocol 2.

Chloramphenicol resistant transductants were selected and the presence of the Ptrc55-pntAB::Cm chromosomal modification was verified by PCR with Ome1151-pntAF (SEQ ID No 37) and Ome1152-pntAR (SEQ ID No 38) (Table 2). The verified and selected strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC:: Gt Ptrc55-pntAB::Cm ΔudhA was called strain 21.

X.3. Construction of Strain 22 by Introduction of pCL1920-PgapA-pycre-TT07 into Strain 21

The pCL1920-PgapA-pycRe-TT07, described previously, was introduced by electroporation into strain 21 (Table 1). The presence of plasmid pCL1920-PgapA-pycRe-TT07 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC Ptrc55-pntAB::Cm ΔudhA pCL1920-PgapA-pycre-TT07 was called strain 22.

XI. Example 11

Construction of Strain 24, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC ΔudhA::Km pCL1920-PgapA-pycRe-TT07

XI.1. Construction of Strain 23 by Transduction of ΔudhA::Km into Strain 10

The ΔudhA::Km deletion described previously was transduced into strain 10 (Table 1) by using a P1 phage lysate from the strain MG1655 metA*11 ΔmetJ Ptrc36-metF ΔudhA::Km pKD46 described above according to Protocol 2.

Kanamycin resistant transductants were selected. The presence of the Ptrc36-ARNmst17-metF promoter modification was verified by PCR (reasons explained in example 6) with primers Ome0726-PtrcmetF-F (SEQ ID No 29) and Ome0727-PtrcmetF-R (SEQ ID No 30) followed by DNA sequencing and the presence of the ΔudhA::Km deletion was verified by PCR with primers Oag0055-udhAF2 (SEQ ID No 33) and Oag0056-udhAR2 (SEQ ID No 34) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC ΔudhA::Km was called strain 23.

XI.2. Construction of Strain 24: Introduction of pCL1920-PgapA-pycre-TT07 into Strain 23

The pCL1920-PgapA-pycRe-TT07, described previously, was introduced by electroporation into strain 23 (Table 1). The presence of plasmid pCL1920-PgapA-pycRe-TT07 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC ΔudhA::Km pCL1920-PgapA-pycre-TT07 was called strain 24.

XII. Example 12

Production of L-methionine by Fermentation in Shake Flasks

Production strains were assessed in small Erlenmeyer flasks. A 5.5 mL preculture was grown at 30° C. for 21 hours in a mixed medium (10% LB medium (LB Broth Miller 25 g/L) with 2.5 g·L$^{-1}$ glucose and 90% minimal medium PC1). It was used to inoculate a 50 mL culture of PC1 medium to an OD$_{600}$ of 0.2. When necessary, antibiotics were added at concentrations of 50 mg·L$^{-1}$ for kanamycin and spectinomycin, 30 mg·L$^{-1}$ for chloramphenicol and 10 mg·L$^{-1}$ for gentamycin. The temperature of the culture was maintained at 37° C. for two hours, 42° C. for two hours and then 37° C. until the end of the culture. When the culture had reached an OD$_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation. For each strain, several repetitions were made.

TABLE 3

Minimal medium composition (PC1).

| Compound | Concentration (g · L$^{-1}$) |
|---|---|
| ZnSO$_4$•7H$_2$O | 0.0040 |
| CuCl$_2$•2H$_2$O | 0.0020 |
| MnSO$_4$•H$_2$O | 0.0200 |
| CoCl$_2$•6H$_2$O | 0.0080 |
| H$_3$BO$_3$ | 0.0010 |
| Na$_2$MoO$_4$•2H$_2$O | 0.0004 |
| MgSO$_4$•7H$_2$O | 1.00 |
| Citric acid | 6.00 |
| CaCl$_2$•2H$_2$O | 0.04 |
| K$_2$HPO$_4$ | 8.00 |
| Na$_2$HPO$_4$ | 2.00 |
| (NH$_4$)$_2$HPO$_4$ | 8.00 |
| NH$_4$Cl | 0.13 |
| NaOH 4M | Adjusted to pH 6.8 |
| FeSO$_4$.7H$_2$O | 0.04 |
| Thiamine | 0.01 |
| Glucose | 15.00 |
| Ammonium thiosulfate | 5.60 |
| Vitamin B12 | 0.01 |
| MOPS | 15.00 |

TABLE 4

Methionine yield (Y$_{met}$), in % g of methionine per g of glucose produced in batch culture by the different strains. For the definition of methionine/glucose yield see below. SD denotes the standard deviation for the yields that was calculated on the basis of several repetitions (N = number of repetitions).

| Strain | Y$_{met}$ | SD |
|---|---|---|
| Strain 7 | 7.27 | 0.12 |
| N = 3 | | |
| Strain 9 | 9.94 | 0.90 |
| N = 6 | | |
| Strain 14 | 10.25 | 0.51 |
| N = 6 | | |
| Strain 10 | 9.75 | 1.29 |
| N = 110 | | |
| Strain 13 | 12.09 | 0.71 |
| N = 9 | | |
| Strain 15 | 12.88 | 0.54 |
| N = 6 | | |
| Strain 24 | 11.41 | 0.18 |
| N = 3 | | |
| Strain 12 | 12.65 | 0.10 |
| N = 3 | | |

The extracellular methionine concentration was quantified by HPLC after OPA/FMOC derivatization. The residual glucose concentration was analyzed using HPLC with refractometric detection. Methionine yield was expressed as follows:

$$Y_{met} = \frac{methionine(g)}{consummed\ glucose\ (g)} * 100$$

As can be seen in table 4 methionine/glucose yield (Y$_{met}$) is increased upon pntAB overexpression and/or udhA deletion (strains 9 and 14 compared to strain 7 and strains 12, 13, 15 and 24 compared to strain 10).

The improvement of the yield is even better upon strong overexpression of the metF gene. Strain 13 that contains both an mRNA stabilizing sequence in front of the metF gene and overexpression of pntAB and udhA deletion shows a higher yield than strain 14 without a strong overexpression of the C1 pathway.

XIII. Example 13

Transhydrogenase and 5,10-methylenetetrahydrofolate Reductase Activities

Results described in example 12, table 4 are confirmed by the analysis of transhydrogenase and 5,10-methylenetetrahydrofolate reductase activities carried out by PntAB and MetF, respectively (Table 5). In small Erlenmeyer flask cultures, both activities increase upon overexpression.

TABLE 5

Transhydrogenase (TH, PntAB) and 5,10-methylenetetrahydrofolate reductase (MTHFR, MetF) activities were determined in the above described strains and are given in mUI/mg of proteins (N = number of independent Erlenmeyer flask cultures).

| Strain | TH | MTHFR |
|---|---|---|
| Strain 7 (N = 3) | 48 ± 2 | 8 ± 4 |
| Strain 9 (N = 3) | 802 ± 43 | 15 ± 5 |
| Strain 14 (N = 3) | 799 ± 75 | 5 ± 1 |
| Strain 10 (N = 3) | 36 ± 4 | 69 ± 3 |
| Strain 13 (N = 9) | 665 ± 35 | 94 ± 7 |
| Strain 15 (N = 3) | 629 ± 37 | 75 ± 8 |
| Strain 24 (N = 3) | 29 ± 4 | ND |
| Strain 12 (N = 3) | 582 ± 27 | ND |

For the in vitro determination of enzyme activities, *E. coli* strains were cultured in minimal medium as described above. Preceding extraction method, cells were harvested from culture broth by centrifugation. The pellet was resuspended in cold 20 mM potassium phosphate buffer (pH 7.2) and cells were lysed by bead beating with a Precellys (Bertin Technologies; 2×10 s at 5000 rpm, 2 minutes on ice between the two steps) followed by centrifugation at 12000 g (4° C.) for 30 minutes. The supernatant was desalted and used for analysis. Protein concentrations were determined using Bradford assay reagent.

Transhydrogenase activities (TH) were assayed as previously described (Yamaguchi and Stout, 2003). Cyclic transhydrogenase activity was assayed spectrophotometrically for 30 minutes at 375 nm in a 37° C. reaction mixture containing 50 mM MES-KOH buffer (pH 6.0), 0.2 mM NADH, 0.2 mM AcPyAD with or without 10 µM NADPH and 6 µg of crude cell extract. All results are the average of at least three measurements.

5,10-methylenetetrahydrofolate reductase activities (MTHFR) were assayed as previously described (Matthews, 1986) with some modifications. The method is shown in equation (1).

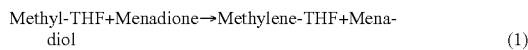

Methyl-THF+Menadione→Methylene-THF+Menadiol       (1)

Methyl-THF is used as the substrate and the formation of methylene-THF is measured by acid decomposition of methylene-THF which yields formaldehyde. The produced formaldehyde reacts with the indicator NBDH to form a highly fluorescent hydrazone derivative at 530 nm. 5,10-methylenetetrahydrofolate reductase activity was assayed for 30 minutes at 37° C. in a reaction mixture containing 50 mM potassium phosphate buffer (pH 6.7), 0.3 mM EDTA, 0.2% (w/v) bovine serum albumin, saturated solution of menadione in 20% methanol/80% $H_2O$, and 20 µg of crude cell extract. After incubation, the reaction is terminated by addition of sodium acetate buffer (pH 4.7) and by placing the tube in a heater block at 100° C. for 2 minutes. After centrifugation for 5 minutes at 10000 g, the produced formaldehyde is measured by addition of 0.001% NBDH in 95% ethanol/6% phosphoric acid with a FLx800 Fluorescence Microplate Reader (Biotek).

XIV. Example 14

Production of L-methionine by Fermentation in Bio-Reactor

Strains that produced substantial amounts of metabolites of interest were subsequently tested under production conditions in 2.5 L fermentors (Pierre Guerin) using a fedbatch strategy.

Briefly, an 24 hours culture grown in 10 mL LB medium with 2.5 g·L$^{-1}$ glucose was used to inoculate a 24 hours preculture in minimal medium (B1a). These incubations were carried out in 500 mL baffled flasks containing 50 mL of minimal medium (B1a) in a rotary shaker (200 RPM). The first preculture was realized at a temperature of 30° C., the second one at a temperature of 34° C.

A third preculture step was carried out in bio-reactors (Sixfors) filled with 200 mL of minimal medium (B1b) inoculated to a biomass concentration of 1.2 g·L$^{-1}$ with 5 mL concentrated preculture. The preculture temperature was maintained constant at 34° C. and the pH was automatically adjusted to a value of 6.8 using a 10% $NH_4OH$ solution. The dissolved oxygen concentration was continuously adjusted to a value of 30% of the partial air pressure saturation with air supply and/or agitation. After glucose exhaustion from the batch medium, the fedbatch was started with an initial flow rate of 0.7 mL·h$^{-1}$, increased exponentially for 24 hours with a growth rate of 0.13 h$^{-1}$ in order to obtain a final cellular concentration of about 18 g·L$^{-1}$.

TABLE 6

Preculture batch mineral medium composition (B1a and B1b).

| Compound | B1a Concentration (g · L$^{-1}$) | B1b Concentration (g · L$^{-1}$) |
|---|---|---|
| Zn(CH$_3$COO)$_2$•2H$_2$O | 0.0130 | 0.0130 |
| CuCl$_2$•2H$_2$O | 0.0015 | 0.0015 |
| MnCl$_2$•4H$_2$O | 0.0150 | 0.0150 |
| CoCl$_2$•6H$_2$O | 0.0025 | 0.0025 |
| H$_3$BO$_3$ | 0.0030 | 0.0030 |
| Na$_2$MoO$_4$•2H$_2$O | 0.0025 | 0.0025 |
| Fe(III) citrate H$_2$O | 0.1064 | 0.1064 |
| EDTA | 0.0084 | 0.0084 |
| MgSO$_4$•7H$_2$O | 1.00 | 1.00 |
| CaCl$_2$•2H$_2$O | 0.08 | 0.08 |
| Citric acid | 1.70 | 1.70 |
| KH$_2$PO$_4$ | 4.57 | 4.57 |
| K$_2$HPO$_4$•3H$_2$O | 2.50 | 2.50 |
| (NH$_4$)$_2$HPO$_4$ | 1.10 | 1.10 |
| (NH$_4$)$_2$SO$_4$ | 4.90 | 4.90 |
| (NH$_4$)$_2$S$_2$O$_3$ | 1.00 | 1.00 |
| Thiamine | 0.01 | 0.01 |
| Vitamin B12 | 0.01 | 0.01 |
| Glucose | 30.00 | 5.00 |
| MOPS | 30.00 | 0.00 |
| NH$_4$OH 28% | Adjusted to pH 6.8 | Adjusted to pH 6.8 |

TABLE 7

Preculture fedbatch mineral medium composition (F1)

| Compound | Concentration (g · L$^{-1}$) |
|---|---|
| Zn(CH$_3$COO)$_2$•H$_2$O | 0.0104 |
| CuCl$_2$•2H$_2$O | 0.0012 |
| MnCl$_2$•4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0424 |
| EDTA | 0.0067 |
| MgSO$_4$ | 5.00 |
| (NH$_4$)$_2$SO$_4$ | 8.30 |
| Na$_2$SO$_4$ | 8.90 |
| (NH$_4$)$_2$S$_2$O$_3$ | 24.80 |
| Thiamine | 0.01 |
| Glucose | 500.00 |
| Vitamin B12 | 0.01 |
| NH$_4$OH 28% | Adjusted to pH 6.8 |

TABLE 8

Culture batch mineral medium composition (B2).

| Compound | Concentration (g · L$^{-1}$) |
|---|---|
| Zn(CH$_3$COO)$_2$•2H$_2$O | 0.0130 |
| CuCl$_2$•2H$_2$O | 0.0015 |
| MnCl$_2$•4H$_2$O | 0.0150 |
| CoCl$_2$•6H$_2$O | 0.0025 |
| H$_3$BO$_3$ | 0.0030 |
| Na$_2$MoO$_4$•2H$_2$O | 0.0025 |
| Fe(III) citrate H$_2$O | 0.1064 |
| EDTA | 0.0084 |
| MgS$_2$O$_3$•6H$_2$O | 1.00 |
| CaCl$_2$•2H$_2$O | 0.08 |
| Citric acid | 1.70 |
| KH$_2$PO$_4$ | 2.97 |
| K$_2$HPO$_4$•3H$_2$O | 1.65 |
| (NH$_4$)$_2$HPO$_4$ | 0.72 |
| (NH$_4$)$_2$S$_2$O$_3$ | 3.74 |
| Thiamine | 0.01 |
| Vitamin B12 | 0.01 |
| Biotin | 0.10 |
| Glucose | 10 |
| NH$_4$OH 28% | Adjusted to pH 6.8 |

TABLE 9

Culture fedbatch medium composition (F2)

| Compound | Concentration (g · L$^{-1}$) |
|---|---|
| Zn(CH$_3$COO)$_2$•2H$_2$O | 0.0104 |
| CuCl$_2$•2H$_2$O | 0.0012 |
| MnCl$_2$•4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0524 |
| EDTA | 0.0067 |
| MgS$_2$O$_3$•6H$_2$O | 10.20 |
| (NH$_4$)$_2$S$_2$O$_3$ | 55.50 |
| Thiamine | 0.01 |
| Vitamin B12 | 0.01 |
| Biotin | 0.10 |
| Glucose | 500 |

Subsequently, 2.5 L fermentors (Pierre Guerin) were filled with 600 mL of minimal medium (B2) and were inoculated to a biomass concentration of 2.1 g·L$^{-1}$ with a preculture volume ranging between 55 to 70 mL.

The culture temperature was maintained constant at 37° C. and pH was maintained to the working value (6.8) by automatic addition of NH$_4$OH solutions (NH$_4$OH 10% for 9 hours and NH$_4$OH 28% until the culture end). The initial agitation rate was set at 200 RPM during the batch phase and was increased up to 1000 RPM during the fedbatch phase. The initial airflow rate was set at 40 NL·h$^{-1}$ during the batch phase and was augmented to 100 NL·h$^{-1}$ at the beginning of the fedbatch phase. The dissolved oxygen concentration was maintained at values between 20 and 40%, preferentially 30% saturation by increasing the agitation.

When the cell mass reached a concentration close to 5 g·L$^{-1}$, the fedbatch was started with an initial flow rate of 5 mL·h$^{-1}$. Feeding solution was injected according to a sigmoid profile with an increasing flow rate that reached 24 mL·h$^{-1}$ after 26 hours of growth. The precise feeding conditions were calculated by the equation:

$$Q(t) = p1 + \frac{p2}{1 + e^{-p3(t-p4)}}$$

where Q(t) is the feeding flow rate in mL·h$^{-1}$ for a batch volume of 600 mL with p1=1.80, p2=22.40, p3=0.270, p4=6.5.

After 26 hours, the fedbatch feeding solution pump was stopped and culture was finalized after glucose exhaustion.

Extracellular amino acids were quantified by HPLC after OPA/Fmoc derivatization and other relevant metabolites were analyzed using HPLC with refractometric detection (organic acids and glucose) and GC-MS after silylation.

TABLE 10

Maximal methionine yield ($Y_{met\ max}$) in % g of methionine per g of glucose produced in fedbatch culture by the different strains. For the definition of methionine/glucose yield see below. SD denotes the standard deviation for the yields which was calculated on the basis of several repetitions (N = number of repetitions).

| Strain | $Y_{met\ max}$ | SD |
|---|---|---|
| Strain 10* N = 5 | 16.94 | 0.86 |
| Strain 13* N = 3 | 20.72 | 0.60 |
| Strain 12 N = 2 | 22.39 | 0.46 |
| Strain 15 N = 1 | 22.27 | Nd |
| Strain 22 N = 1 | 23.68 | Nd |
| Strain 18 N = 3 | 23.69 | 0.52 |
| Strain 20 N = 1 | 22.57 | Nd |

*Strains 10 and 13 were cultivated with respectively 49.1 and 55.5 g · L$^{-1}$ of ammonium thiosulfate and with 5 g · L$^{-1}$ of magnesium sulphate instead of magnesium thiosulfate in fedbatch medium. The batch medium contained 1 g · L$^{-1}$ of magnesium sulphate instead of magnesium thiosulfate for the two strains.

As observed previously in flask experiments, in the same way, in bioreactor, methionine/glucose yield ($Y_{met\ max}$) is increased upon pntAB overexpression and/or udhA deletion (compare strains 10 and 13 of table 10).

Moreover we show that a fine tuned regulation of pntAB overexpression improved methionine production as can be seen with strains 12, 15, 18, 20 and 22 of table 10 above.

Methionine production is modulated by the expression level of the pntAB genes and we show that it is better with a moderate overexpression of pntAB.

The fermentor volume was calculated by adding to the initial volume the amount of solutions added to regulate the pH and to feed the culture and by subtracting the volume used for sampling and lost by evaporation.

The fedbatch volume was followed continuously by weighing the feeding stock. The amount of injected glucose was then calculated on the basis of the injected weight, the density of the solution and the glucose concentration determined by the method of Brix ([Glucose]). The methionine yield was expressed as followed:

$$Y_{met} = \frac{\text{Methionine}_t * V_t - \text{Methionine}_0 * V_0 \times 100}{\text{Consumed glucose}_t}$$

The maximal yield obtained during the culture was presented here for each strain.

With Methionine$_0$ and Methionine$_t$ respectively the initial and final methionine concentrations and V$_0$ and V$_t$ the initial and the instant t volumes.

The consumed glucose was calculated as follows:

$$\text{fed volume}_t = \frac{\text{fed weight}_0 - \text{fed weight}_t}{\text{density fed solution}}$$

Injected Glucose$_t$=fed volume$_t$*[Glucose]

Consumed glucose$_t$=[Glucose]$_0$*V$_0$+Injected Glucose-[Glucose]$_{residual}$*V$_t$With [Glucose]$_0$,[Glucose],[Glucose]$_{residual}$ respectively the initial, the fed and the residual glucose concentrations.

XV. Example 15

Transhydrogenase Activity

Results described in example 14, table 10 are confirmed by the analysis of transhydrogenase activities carried out by PntAB (Table 11). As observed previously in flask experiments, transhydrogenase activities are increased upon pntAB overexpression (see strains 10 and 13 of table 11). Moreover, a fine tuned regulation of pntAB overexpression decreased about 10 times the transhydrogenase activities as can be seen with strain 18 of table 11.

TABLE 11

Transhydrogenase (TH, PntAB) activities were determined in the above described strains and are given in mUI/mg of proteins (N = minimum two points of independent fermentor cultures).

| Strain | TH |
|---|---|
| Strain 10 (N = 3) | 0.4 ± 0.5 |
| Strain 13 (N = 7) | 1493 ± 134 |
| Strain 12 (N = 9) | 1288 ± 128 |
| Strain 15 (N = 9) | 1271 ± 61 |
| Strain 18 (N = 6) | 130 ± 18 |

Transhydrogenase activities (TH) were assayed as previously described in Example 13. All results are the average of at least three measurements.

REFERENCES

Saunderson, C. L., (1985) *British Journal of Nutrition* 54, 621-633

Ouzonis, C. A., and Karp, P. D. (2000) *Genome Res.* 10, 568-576

Verho et al., (2003) *Applied and Environmental Microbiology* 69, 5892-5897

Chemler et al., (2007) *Applied and Environmental Microbiology* 77, 797-807

Alper, H. et al., (2005) *Metab. Eng.* 7, 155-164

Kelle T et al., (2005) *L-lysine production; In: Eggeling L, Bott M (eds) Handbook of corynebacterium glutamicum.* CRC, Boca Raton, pp 467-490

Sauer U, Canonaco F, Heri S, Perrenoud A, Fischer E., "*The soluble and membrane-bound transhydrogenases UdhA and PntAB have divergent functions in NADPH metabolism of Escherichia coli.*", 2004, *JBC*, 279:6613-6619

Jackson J B, "*Proton translocation by transhydrogenase.*", 2003, *FEBS Lett* 545:18-24

Moreira dos Santos M, Raghevendran V, Kötter P, Olsson L, Nielsen J. *Metab Eng.* 2004 October; 6(4):352-63, "*Manipulation of malic enzyme in Saccharomyces cerevisiae for increasing NADPH production capacity aerobically in different cellular compartments.*"

Weckbecker and Hummel, *Biotechnol Lett.* 2004 November; 26(22):1739-44, "*Improved synthesis of chiral alcohols with Escherichia coli cells co-expressing pyridine nucleotide transhydrogenase, NADP+-dependent alcohol dehydrogenase and NAD+-dependent formate dehydrogenase*"

Sanchez A M, Andrews J, Hussein I, Bennett G N, San K Y., *Biotechnol Prog.* 2006 March-April; 22(2):420-5, "*Effect of overexpression of a soluble pyridine nucleotide transhydrogenase (UdhA) on the production of poly(3-hydroxybutyrate) in Escherichia coli.*"

Datsenko, K. A. & Wanner, B. L. (2000) "*One-step inactivation of chromosomal genes in Escherichia coli K-12 using PCR products*". *Proc. Natl. Acad. Sci. USA* 97: 6640-6645

Carrier and Keasling (1998) *Biotechnol. Prog.* 15, 58-64

Amann E, Brosius J, Ptashne M., *Gene.* 1983 November; 25(2-3): 167-78, "*Gene Vectors bearing a hybrid trp-lac promoter useful for regulated expression of cloned genes in Escherichia coli.*"

Amann E, Ochs B, Abel K J. *Gene.* 1988 Sep. 30; 69(2):301-15. "*Tightly regulated tac promoter vectors useful for the expression of unfused and fused proteins in Escherichia coli.*"

Hawley & McClure, *Nucleic Acids Res.* 1983 Apr. 25; 11(8): 2237-55. "*Compilation and analysis of Escherichia coli promoter DNA sequences*".

Anderson, 1946, *Proc. Natl. Acad. Sci. USA* 32:120-128

Miller, 1992; "*A Short Course in Bacterial Genetics: A Laboratory Manual and Handbook for Escherichia coli and Related Bacteria*", Cold Spring Harbor Laboratory Press, Cold Spring Harbor, N.Y.

Schaefer et al. 1999, *Anal. Biochem.* 270: 88-96

Liebl et al., 1989, *Appl. Microbiol. Biotechnol.* 32: 205-210

Riedel et al. 2001, *J. Mol. Microbiol. Biotechnol.* 3: 573-583

Dennis & Zyltra, *AEM* July 1998, p 2710-2715

Mermet-Bouvier & Chauvat, 1994, *Current Microbiology*, vol. 28, pp 145-148

Tsurimoto T, Hase T, Matsubara H, Matsubara K, *Mol Gen Genet.* 1982; 187(1):79-86

Orosz A, Boros I and Venetianer P. *Eur. J. Biochem.* 1991 Nov. 1; 201(3):653-9

Norrander et al., 1983, *Gene* 26, 101-106

Harrington K. J., Laughlin R. B. and Liang S. *Proc Natl Acad Sci USA.* 2001 Apr. 24; 98(9):5019-24.

The invention claimed is:

1. A microorganism modified for an improved production of methionine, wherein said microorganism is modified to enhance transhydrogenase activity of PntAB by overexpressing the genes encoding PntAB.

2. The microorganism of claim 1, wherein said microorganism is modified to attenuate activity of transhydrogenase UdhA by deleting the gene encoding UdhA.

3. The microorganism of claim 1, wherein said microorganism is modified to increase one carbon metabolism by enhancing at least one of the following activities:
   a. activity of methylenetetrahydrofolate reductase, MetF;
   b. activity of glycine cleavage complex, GcvTHP and Lpd;
   c. activity of serine hydroxymethyltransferase, GlyA; and/or
   d. activity of methyltransferase, MetH or MetE.

4. The microorganism of claim 3, wherein said activity of MetF is enhanced by overexpressing the metF gene and/or by optimizing its translation by using a RNA stabiliser.

5. The microorganism of claim 4, wherein said metF gene is under control of a strong promoter comprising at least one Ptrc family promoter.

6. The microorganism of claim 1, wherein expression of at least one of the following genes is increased: cysP, cysU, cysW, cysA, cysM, cysI, cysJ, cysH, cysE, serA, serB, serC, metA allele with reduced feed-back sensitivity, thrA or thrA allele with reduced feed-back sensitivity.

7. The microorganism of claim 6, wherein at least one of said genes is under control of an inducible promoter.

8. The microorganism of claim 1, wherein expression of the gene coding for pyruvate carboxylase is enhanced.

9. The microorganism of claim 1, wherein expression of at least one of the following genes of said microorganism is attenuated: pykA, pykF, purU, yncA or metJ.

10. The microorganism of claim 1, wherein said microorganism is selected from Enterobacteriaceae and Corynebacteriaceae.

11. The microorganism of claim 10, wherein said microorganism is selected from *Escherichia, Klebsiella* and *Corynebacterium*.

12. The microorganism of claim 2, wherein said microorganism is modified to increase one carbon metabolism by enhancing at least one of the following activities:
   a. the activity of methylenetetrahydrofolate reductase, MetF;
   b. activity of glycine cleavage complex, GcvTHP and Lpd;
   c. activity of serine hydroxymethyltransferase, GlyA; and/or
   d. activity of methyltransferase, MetH or MetE.

13. The microorganism of claim 3, wherein expression of at least one of the following genes is increased: cysP, cysU, cysW, cysA, cysM, cysI, cysJ, cysH, cysE, serA, serB, serC, metA allele with reduced feed-back sensitivity, thrA or thrA allele with reduced feed-back sensitivity.

14. The microorganism of claim 2, wherein expression of the gene coding for pyruvate carboxylase is enhanced.

15. The microorganism of claim 2, wherein expression of at least one the following genes of the microorganism is attenuated: pykA, pykF, purU, yncA or metJ.

16. The microorganism of claim 2, wherein said microorganism is selected from Enterobacteriaceae and Corynebacteriaceae.

17. The microorganism of claim 16, wherein said microorganism is selected from *Escherichia, Klebsiella* and *Corynebacterium*.

18. The microorganism of claim 17, wherein said microorganism is *Escherichia coli*.

19. The microorganism of claim 17, wherein said microorganism is *Corynebacterium glutamicum*.

* * * * *

SEQUENCE LISTING

<160> NUMBER OF SEQ ID NOS: 51

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide

<400> SEQUENCE: 1
ggtattccac gggattttc gcg                                             23

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide

<400> SEQUENCE: 2
cgtcagtaat cacattgcct gttgg                                          25

<210> SEQ ID NO 3
<211> LENGTH: 122
<212> TYPE: DNA
<213> ORGANISM: Artificial Sequence
<220> FEATURE:
<223> OTHER INFORMATION: Oligonucleotide

<400> SEQUENCE: 3
acgttaaatc tatcaccgca aggataaat atctaacacc gtgcgtgttg acaattttac     60
ctctggcggt gataatggtt gcatgtacta aggaggttat aaatgagagt gttgaagttc    120
gg                                                                   122

<210> SEQ ID NO 4
<211> LENGTH: 88
<212> TYPE: DNA
<213> ORGANISM: Artificial Sequence
<220> FEATURE:
<223> OTHER INFORMATION: Oligonucleotide

<400> SEQUENCE: 4
taaaaaaaat aagagttacc atttaaggta actcttattt ttagggcccg gtacccagct    60
tttgttccct ttagtgaggg ttaattgc                                       88

<210> SEQ ID NO 5
<211> LENGTH: 50
<212> TYPE: DNA
<213> ORGANISM: Artificial Sequence
<220> FEATURE:
<223> OTHER INFORMATION: Oligonucleotide

<400> SEQUENCE: 5
cgtagttaac gaattcgact agaaagtatg tgagcaacta tcggcccccc                50

<210> SEQ ID NO 6
<211> LENGTH: 88
<212> TYPE: DNA
<213> ORGANISM: Artificial Sequence
<220> FEATURE:
<223> OTHER INFORMATION: Oligonucleotide

<400> SEQUENCE: 6
gcttgtatac aacagataaa acgaaaggcc cagtctttcg actgagcctt tcgttttatt    60

-continued tgatgaggct gcgctacggc actcacgg                                              88

<210> SEQ ID NO 7
<211> LENGTH: 82
<212> TYPE: DNA
<213> ORGANISM: Artificial Sequence
<220> FEATURE:
<223> OTHER INFORMATION: Oligonucleotide

<400> SEQUENCE: 7
agactgggcc tttcgtttta tctgttgtat acaagcttaa ttaagggccc gggcggatcc          60
cccaaaacaa agcccggttc gc                                                    82

<210> SEQ ID NO 8
<211> LENGTH: 36
<212> TYPE: DNA
<213> ORGANISM: Artificial Sequence
<220> FEATURE:
<223> OTHER INFORMATION: Oligonucleotide

<400> SEQUENCE: 8
cgtagttaac gaattcagct gatattcgcc acgggc                                     36

<210> SEQ ID NO 9
<211> LENGTH: 35
<212> TYPE: DNA
<213> ORGANISM: Artificial Sequence
<220> FEATURE:
<223> OTHER INFORMATION: Oligonucleotide

<400> SEQUENCE: 9
tcccccgggg tatactgtag gctggagctg cttcg                                      35

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide

<400> SEQUENCE: 10
gcccaagctt catatgaata tcctccttag                                            30

<210> SEQ ID NO 11
<211> LENGTH: 19
<212> TYPE: DNA
<213> ORGANISM: Artificial Sequence
<220> FEATURE:
<223> OTHER INFORMATION: Oligonucleotide

<400> SEQUENCE: 11
gggctgatgc tgattgaac                                                        19

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide

<400> SEQUENCE: 12
gtgttaccga cgccgtaaac gg                                                    22

<210> SEQ ID NO 13

```
<211> LENGTH: 128
<212> TYPE: DNA
<213> ORGANISM: Artificial Sequence
<220> FEATURE:
<223> OTHER INFORMATION: Oligonucleotide

<400> SEQUENCE: 13
gcaagctagc tcactcgttg agaggaagac gaaaatgact ccgtttatga ctgaagattt    60
cctgttagat accgtcacac tggctcacct tcgggtgggc ctttctgctg taggctggag   120
ctgcttcg                                                            128

<210> SEQ ID NO 14
<211> LENGTH: 129
<212> TYPE: DNA
<213> ORGANISM: Artificial Sequence
<220> FEATURE:
<223> OTHER INFORMATION: Oligonucleotide

<400> SEQUENCE: 14
ttaacaactc atttcgactt tatagcgtta cgccgctttt gaagatcgcc gaattcgagc    60
tcggtacccg gggatccatc tcgagatccg cggatgtata catgggcccc atatgaatat   120
cctccttag                                                           129

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide

<400> SEQUENCE: 15
ggtgtggtgg aaaattcgtc g                                              21

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
gcattacgat tgcccatacc                                                20

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide

<400> SEQUENCE: 17
cccactggcc tgtaatatgt tcgg                                           24

<210> SEQ ID NO 18
<211> LENGTH: 34
<212> TYPE: DNA
<213> ORGANISM: Artificial Sequence
<220> FEATURE:
<223> OTHER INFORMATION: Oligonucleotide

<400> SEQUENCE: 18
atgcgatatc gaccgtataa gcagcagaat aggc                                34
```

<210> SEQ ID NO 19
<211> LENGTH: 2218
<212> TYPE: DNA
<213> ORGANISM: Artificial Sequence
<220> FEATURE:
<223> OTHER INFORMATION: DCP4-6::TT02-MCS::Km fragment

<400> SEQUENCE: 19

```
ggcgcgccag gcctagggcc gacgatgtac gtcaggtgtg caacctcgcc gatccggtgg      60
ggcaggtaat cgatggcggc gtactggaca gcggcctgcg tcttgagcgt cgtcgcgtac     120
cgctggggt tattggcgtg atttatgaag cgcgcccgaa cgtgacggtt gatgtcgctt      180
cgctgtgcct gaaaaccggt aatgcggtga tcctgcgcgg tggcaaagaa acgtgtcgca     240
ctaacgctgc aacggtggcg gtgattcagg acgccctgaa atcctgcggc ttaccggcgg     300
gtgccgtgca ggcgattgat aatcctgacc gtgcgctggt cagtgaaatg ctgcgtatgg     360
ataaatacat cgacatgctg atcccgcgtg gtggcgctgg tttgcataaa ctgtgccgtg     420
aacagtcgac aatcccggtg atcacaggtg gtataggcgt atgccatatt tacgttgatg     480
aaagtgtaga gatcgctgaa gcattaaaag tgatcgtcaa cgcgaaaact cagcgtccga     540
gcacatgtaa tacggttgaa acgttgctgg tgaataaaaa catcgccgat agcttcctgc     600
ccgcattaag caaacaaatg gcggaaagcg gcgtgacatt acacgcagat gcagctgcac     660
tggcgcagtt gcaggcaggc cctgcgaagg tggttgctgt taaagccgaa gagtatgacg     720
atgagtttct gtcattagat ttgaacgtca aaatcgtcag cgatcttgac gatgccatcg     780
cccatattcg tgaacacggc acacaacact ccgatgcgat cctgacccgc gatatgcgca     840
acgcccagcg ttttgttaac gaagtggatt cgtccgctgt ttacgttaac gcctctacgc     900
gttttaccga cggcggccag tttggtctgg gtgcggaagt ggcggtaagc acacaaaaac     960
tccacgcgcg tggcccaatg gggctggaag cactgaccac ttacaagtgg atcggcattg    1020
gtgattacac cattcgtgcg taacatcaaa taaaacgaaa ggctcagtcg aaagactggg    1080
cctttcgttt tatctgttgt atacaagctt aataagggcc cgggcggatc ccaccacgtt    1140
tcctcctgtg ccgtatttgt gccattgtaa ccttggcaat tcatcaaaat actgttctga    1200
catcaggcag tgcaggtgca gacatttaag ccaattgctg ccgccattct ttgacgtagt    1260
caatcagggc gcggagcttt ggtgcaatat tgcgacgctg tgggaaatac agatagaagc    1320
ccggaaattg tggaagaaag tcatcaagca gcgatacaag tttaccgctt caatatatg     1380
gcctgaaagt ttcctgagtg caattgtta ttcctccgcc ggcaagagcc agcctcaaca     1440
tcagacgcag atcattagtc gtaatctgcg gttcaatcgc aaggtcgaaa gttctcccgt    1500
tttcttcaaa tggccagcga taaggcgcaa cctccgggga ctgacgccag ccgatacact    1560
tatgggtatt tcccccggag gcgagaaagc actctccacg cccggccgca aggatcagga    1620
cgacggggc aggcatgaat cctcctcctg atggagacgt acagaggcga cttctgccag    1680
cacgagagt gccagagtat gcgcatcccg ggctttgggg aatatcccga cgggtgcccg    1740
gatttgcgtt gtttcctccc tggaccatcc cagctcgtgg agcttttgca gacgtaacgt    1800
gtgggttcga tagctgccca atgcgccgag ataaagggt tttgcttctc gcgcggcctg    1860
caacactggc agctcccggt tgagatcatg gcacagcaaa atgaccgccg tatcggtatc    1920
gatctgagcg ctggctgagg ccggaaaaag atcgaagata tggctgtcat agcctgtggc    1980
tgctgcaaga ctcgcggttg cctgcgcctc aagagaacgt ccgtaaatca tcagcctgac    2040
gcatggcctg aaccccacct caaagccatt gagattccag cccgtccggg tttgcgtggg    2100
```

```
caggcacacc agcgattgtg cttgcggatc gtagcgcagc cccaccggtt ttctctgttc    2160
caggcggttc agcacggcga gcagaggctg tgccgagcgt agggtacctc ttaattaa     2218

<210> SEQ ID NO 20
<211> LENGTH: 35
<212> TYPE: DNA
<213> ORGANISM: Artificial Sequence
<220> FEATURE:
<223> OTHER INFORMATION: Oligonucleotide

<400> SEQUENCE: 20
tcccccgggg tataccatat gaatatcctc cttag                              35

<210> SEQ ID NO 21
<211> LENGTH: 30
<212> TYPE: DNA
<213> ORGANISM: Artificial Sequence
<220> FEATURE:
<223> OTHER INFORMATION: Oligonucleotide

<400> SEQUENCE: 21
gcccaagctt tgtaggctgg agctgcttcg                                    30

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide

<400> SEQUENCE: 22
gctcgcagat ggttggcaac                                               20

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide

<400> SEQUENCE: 23
tggagatgat gggctcaggc                                               20

<210> SEQ ID NO 24
<211> LENGTH: 1156
<212> TYPE: DNA
<213> ORGANISM: Artificial Sequence
<220> FEATURE:
<223> OTHER INFORMATION: DtreBC::TT02-MCS fragment

<400> SEQUENCE: 24
ggcgcgccgg caatcaaaat cctgatgcaa cggctgtatg accaggggca tcgtaatatc    60
agttatctcg gcgtgccgca cagtgacgtg acaaccggta agcgacgtca cgaagcctac   120
ctggcgttct gcaaagcgca taaactgcat cccgttgccg ccctgccagg gcttgctatg   180
aagcaaggct atgagaacgt tgcaaaagtg attacgcctg aaactaccgc cttactgtgc   240
gcaaccgaca cgctggcact ggcgcaagt aaataccctgc aagagcaacg catcgacacc   300
ttgcaactgg cgagcgtcgg taatacgccg ttaatgaaat cctccatcc ggagatcgta   360 accgtagatc ccggttacgc cgaagctgga cgccaggcgg cttgccagtt gatcgcgcag   420
gtaaccgggc gcagcgaacc gcaacaaatc atcatccccg ccaccctgtc ctgatcgttt   480
cctgaacgat aaattgtgat ctcatcaaat aaaacgaaag gctcagtcga aagactgggc   540
```

```
ctttcgtttt atctgttgta tacaagctta ataagggccc gggcggatcc gtctgtcagt    600
atgttgtttt tgttgatttt tcaaccagca aattcattaa aaaatttaca tatcgctgta    660
gcgcccgtca tccgtacgct ctgcttttta ctttgagcta catcaaaaaa agctcaaaca    720
tccttgatgc aaagcactat atatagactt taaaatgcgt cccaacccaa tatgttgtat    780
taatcgacta taattgctac tacagctccc cacgaaaaag gtgcggcgtt gtggataagc    840
ggatggcgat tgcggaaagc accggaaaac gaaacgaaaa aaccggaaaa cgcctttccc    900
aatttctgtg gataacctgt tcttaaaaat atggagcgat catgacaccg catgtgatga    960
aacgagacgc tgcaaagtg ccgtttaaat cagagcgcat caaagaagcg attctgcgtg    1020
cagctaaagc agcggaagtc gatgatgccg attattgcgc cactgttgcc gcggttgtca    1080
gcgagcagat gcagggccgc aaccaggtgg atatcaatga gatccagacc gcagttgaaa    1140
atcagctgtt aattaa                                                     1156
```

<210> SEQ ID NO 25
<211> LENGTH: 109
<212> TYPE: DNA
<213> ORGANISM: Artificial Sequence
<220> FEATURE:
<223> OTHER INFORMATION: Oligonucleotide

<400> SEQUENCE: 25

```
tccccgggg tatactgtag gctggagctg cttcgaagtt cctatacttt ctagagaata    60
ggaacttcgg aataggaact tcatttagat gggtaccgag ctcgaattg                109
```

<210> SEQ ID NO 26
<211> LENGTH: 101
<212> TYPE: DNA
<213> ORGANISM: Artificial Sequence
<220> FEATURE:
<223> OTHER INFORMATION: Oligonucleotide

<400> SEQUENCE: 26

```
cccaagcttc atatgaatat cctccttagt tcctattccg aagttcctat tctctagaaa    60
gtataggaac ttcggcgcgg atgggtaccg agctcgaatt g                        101
```

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide

<400> SEQUENCE: 27

```
gttgccgaac atttgggagt gc                                              22
```

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide

<400> SEQUENCE: 28

```
ggagatcaga ttcaccacat cc                                              22
```

<210> SEQ ID NO 29
<211> LENGTH: 29
<212> TYPE: DNA

<213> ORGANISM: Artificial Sequence
<220> FEATURE:
<223> OTHER INFORMATION: Oligonucleotide

<400> SEQUENCE: 29
gcccggtact catgttttcg ggtttatgg          29

<210> SEQ ID NO 30
<211> LENGTH: 28
<212> TYPE: DNA
<213> ORGANISM: Artificial Sequence
<220> FEATURE:
<223> OTHER INFORMATION: Oligonucleotide

<400> SEQUENCE: 30
ccgttattcc agtagtcgcg tgcaatgg           28

<210> SEQ ID NO 31
<211> LENGTH: 100
<212> TYPE: DNA
<213> ORGANISM: Artificial Sequence
<220> FEATURE:
<223> OTHER INFORMATION: Oligonucleotide

<400> SEQUENCE: 31
ggtgcgcgcg tcgcagttat cgagcgttat caaaatgttg gcggcggttg cacccactgg     60
ggcaccatcc cgtcgaaagc catatgaata tcctccttag                          100

<210> SEQ ID NO 32
<211> LENGTH: 100
<212> TYPE: DNA
<213> ORGANISM: Artificial Sequence
<220> FEATURE:
<223> OTHER INFORMATION: Oligonucleotide

<400> SEQUENCE: 32
cccagaatct cttttgtttc ccgatggaac aaaattttca gcgtgcccac gttcatgccg     60
acgatttgtg cgcgtgccag tgtaggctgg agctgcttcg                          100

<210> SEQ ID NO 33
<211> LENGTH: 18
<212> TYPE: DNA
<213> ORGANISM: Artificial Sequence
<220> FEATURE:
<223> OTHER INFORMATION: Oligonucleotide

<400> SEQUENCE: 33
gtgaatgaac ggtaacgc                      18

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide

<400> SEQUENCE: 34
gatgctggaa gatggtcact          20

<210> SEQ ID NO 35
<211> LENGTH: 116
<212> TYPE: DNA
<213> ORGANISM: Artificial Sequence
<220> FEATURE:
<223> OTHER INFORMATION: Oligonucleotide

<400> SEQUENCE: 35
gctcgtacat gagcagcttg tgtggctcct gacacaggca aaccatcatc aataaaaccg    60
attcacactg gctcaccttc gggtgggcct ttctgccata tgaatatcct ccttag       116

<210> SEQ ID NO 36
<211> LENGTH: 129
<212> TYPE: DNA
<213> ORGANISM: Artificial Sequence
<220> FEATURE:
<223> OTHER INFORMATION: Oligonucleotide

<400> SEQUENCE: 36
gctgcaacac gggtttcatt ggttaaccgt tctcttggta tgccaattcg catgatattc    60
ccttccttcc acacattata cgagccggat gattaattgt caacagctct gtaggctgga   120
gctgcttcg                                                          129

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
ccactatcac ggctgaatcg                                               20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
gtcccaggat tcagtaacgc                                               20

<210> SEQ ID NO 39
<211> LENGTH: 46
<212> TYPE: DNA
<213> ORGANISM: Artificial Sequence
<220> FEATURE:
<223> OTHER INFORMATION: Oligonucleotide

<400> SEQUENCE: 39
cgtagttaac gaattcctgc gccaccgagc cagccagacc ttgcgc                   46

<210> SEQ ID NO 40
<211> LENGTH: 95
<212> TYPE: DNA
<213> ORGANISM: Artificial Sequence
<220> FEATURE:
<223> OTHER INFORMATION: Oligonucleotide

<400> SEQUENCE: 40
gcttgtatac aacagataaa acgaaaggcc cagtctttcg actgagcctt tcgttttatt    60
tgatggcgtt ctcctctata aagcctgcag caagc                               95

<210> SEQ ID NO 41
<211> LENGTH: 90
<212> TYPE: DNA
<213> ORGANISM: Artificial Sequence
<220> FEATURE:

<223> OTHER INFORMATION: Oligonucleotide

<400> SEQUENCE: 41
agactgggcc tttcgtttta tctgttgtat acaagcttaa ttaagggccc gggcggatcc    60
atttgcgacc attcctggaa aaatggagtc                                    90

<210> SEQ ID NO 42
<211> LENGTH: 47
<212> TYPE: DNA
<213> ORGANISM: Artificial Sequence
<220> FEATURE:
<223> OTHER INFORMATION: Oligonucleotide

<400> SEQUENCE: 42
cgtagttaac gaattccgcc ccttctttca ggttgcgtag gccatac                  47

<210> SEQ ID NO 43
<211> LENGTH: 22
<212> TYPE: DNA
<213> ORGANISM: Artificial Sequence
<220> FEATURE:
<223> OTHER INFORMATION: Oligonucleotide

<400> SEQUENCE: 43
gccgttcaac actggctgga cg                                             22

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide

<400> SEQUENCE: 44
tgccattgca ggtgcatcgc                                                20

<210> SEQ ID NO 45
<211> LENGTH: 53
<212> TYPE: DNA
<213> ORGANISM: Artificial Sequence
<220> FEATURE:
<223> OTHER INFORMATION: Oligonucleotide

<400> SEQUENCE: 45
acgcgtcgac ggtatcgata agcttcgttt aaacaagccc aaaggaagag tga           53

<210> SEQ ID NO 46
<211> LENGTH: 42
<212> TYPE: DNA
<213> ORGANISM: Artificial Sequence
<220> FEATURE:
<223> OTHER INFORMATION: Oligonucleotide

<400> SEQUENCE: 46
gtatcttgga tatgggcata tgttccacca gctatttgtt ag                       42

<210> SEQ ID NO 47
<211> LENGTH: 42
<212> TYPE: DNA
<213> ORGANISM: Artificial Sequence
<220> FEATURE:
<223> OTHER INFORMATION: Oligonucleotide

<400> SEQUENCE: 47
ctaacaaata gctggtggaa catatgccca tatccaagat ac                       42

```
<210> SEQ ID NO 48
<211> LENGTH: 115
<212> TYPE: DNA
<213> ORGANISM: Artificial Sequence
<220> FEATURE:
<223> OTHER INFORMATION: Oligonucleotide

<400> SEQUENCE: 48 tcccccggg gatccgaatt cgcagaaagg cccacccgaa ggtgagccag ctcgagggca      60
aggacgggcg aacgaaacct ttcgtgccgt tcgctcatcc gccgtaaacc gccag         115

<210> SEQ ID NO 49
<211> LENGTH: 129
<212> TYPE: DNA
<213> ORGANISM: Artificial Sequence
<220> FEATURE:
<223> OTHER INFORMATION: Oligonucleotide

<400> SEQUENCE: 49
gctgcaacac gggtttcatt ggttaaccgt tctcttggta tgccaattcg catgatattc    60
ccttccttcc acacagtata cgagccggat gattaatcgt caacagctct gtaggctgga   120
gctgcttcg                                                            129

<210> SEQ ID NO 50
<211> LENGTH: 129
<212> TYPE: DNA
<213> ORGANISM: Artificial Sequence
<220> FEATURE:
<223> OTHER INFORMATION: Oligonucleotide

<400> SEQUENCE: 50
gctgcaacac gggtttcatt ggttaaccgt tctcttggta tgccaattcg catgatattc    60
ccttccttcc acacatttta cgagccggat gattaatagc caacagctct gtaggctgga   120
gctgcttcg                                                            129

<210> SEQ ID NO 51
<211> LENGTH: 129
<212> TYPE: DNA
<213> ORGANISM: Artificial Sequence
<220> FEATURE:
<223> OTHER INFORMATION: Oligonucleotide

<400> SEQUENCE: 51
gctgcaacac gggtttcatt ggttaaccgt tctcttggta tgccaattcg catgatattc    60
ccttccttcc acacactata cgagccggat gattaatggt caacagctct gtaggctgga   120
gctgcttcg                                                            129
```